US008071135B2

(12) United States Patent
Liu et al.

(10) Patent No.: US 8,071,135 B2
(45) Date of Patent: Dec. 6, 2011

(54) PLACENTAL TISSUE COMPOSITIONS

(75) Inventors: Qing Liu, Hillsborough, NJ (US);
Cynthia Ray, Flemington, NJ (US)

(73) Assignee: Anthrogenesis Corporation, Warren, NJ (US)

( * ) Notice: Subject to any disclaimer, the term of this patent is extended or adjusted under 35 U.S.C. 154(b) by 950 days.

(21) Appl. No.: 11/973,125

(22) Filed: Oct. 4, 2007

(65) Prior Publication Data
US 2008/0181967 A1 Jul. 31, 2008

Related U.S. Application Data

(60) Provisional application No. 60/849,521, filed on Oct. 4, 2006.

(51) Int. Cl.
*A61K 35/50* (2006.01)
(52) U.S. Cl. ....................................................... 424/583
(58) Field of Classification Search .................. None
See application file for complete search history.

(56) References Cited

U.S. PATENT DOCUMENTS

| | | | |
|---|---|---|---|
| 3,157,524 A | 11/1964 | Artandi | |
| 3,800,792 A | 4/1974 | McKnight et al. | |
| 4,060,081 A | 11/1977 | Yannas et al. | |
| 4,320,201 A | 3/1982 | Berg et al. | |
| 4,361,552 A | 11/1982 | Baur, Jr. | |
| 4,420,339 A | 12/1983 | Kato | |
| 4,599,226 A | 7/1986 | Fox, Jr. et al. | |
| 4,704,131 A | 11/1987 | Noishiki et al. | |
| 4,772,284 A | 9/1988 | Jefferies et al. | |
| 4,837,285 A | 6/1989 | Berg et al. | |
| 4,973,493 A | 11/1990 | Guire | |
| 5,028,695 A | 7/1991 | Eckmayer et al. | |
| 5,036,056 A | 7/1991 | Kludas | |
| 5,116,620 A | 5/1992 | Chvapil et al. | |
| 5,141,747 A | 8/1992 | Scholz | |
| 5,230,693 A | 7/1993 | Williams et al. | |
| 5,308,889 A | 5/1994 | Rhee et al. | |
| 5,318,780 A * | 6/1994 | Viegas et al. | 424/427 |
| 5,428,022 A | 6/1995 | Palefsky et al. | |
| 5,436,135 A | 7/1995 | Tayot | |
| 5,486,359 A | 1/1996 | Caplan | |
| 5,523,291 A | 6/1996 | Janzen et al. | |
| 5,607,590 A | 3/1997 | Shimizu | |
| 5,612,028 A | 3/1997 | Sackier et al. | |
| 5,618,312 A | 4/1997 | Yui et al. | |
| 5,635,517 A | 6/1997 | Muller | |
| 5,639,796 A | 6/1997 | Lee | |
| 5,656,478 A | 8/1997 | Tanagho et al. | |
| 5,658,582 A | 8/1997 | Dorigatti et al. | |
| 5,686,425 A | 11/1997 | Lee | |
| 5,698,579 A | 12/1997 | Muller | |
| 5,705,488 A | 1/1998 | Janzen et al. | |
| 5,723,010 A | 3/1998 | Yui et al. | |
| 5,739,113 A | 4/1998 | Lee | |
| 5,763,399 A | 6/1998 | Lee | |
| 5,798,368 A | 8/1998 | Muller | |
| 5,814,328 A | 9/1998 | Gunasekaran | |
| 5,830,548 A | 11/1998 | Andersen et al. | |
| 5,837,278 A | 11/1998 | Geistlich et al. | |
| 5,874,448 A | 2/1999 | Muller | |
| 5,876,451 A | 3/1999 | Yui et al. | |
| 5,877,200 A | 3/1999 | Muller | |
| 5,916,266 A | 6/1999 | Yui et al. | |
| 5,929,117 A | 7/1999 | Muller | |
| 5,932,205 A | 8/1999 | Wang et al. | |
| 5,939,323 A | 8/1999 | Valentini et al. | |
| 5,955,476 A | 9/1999 | Muller | |
| 5,993,844 A | 11/1999 | Abraham et al. | |
| 6,093,417 A | 7/2000 | Petrus | |
| 6,113,932 A | 9/2000 | Hoath et al. | |
| 6,124,259 A | 9/2000 | Delmage et al. | |
| 6,143,315 A | 11/2000 | Wang et al. | |
| 6,152,142 A | 11/2000 | Tseng | |
| 6,165,489 A | 12/2000 | Berg et al. | |
| 6,261,549 B1 | 7/2001 | Fernandez | |
| 6,281,230 B1 | 8/2001 | Muller | |
| 6,300,315 B1 | 10/2001 | Liu | |
| 6,316,471 B1 | 11/2001 | Muller | |
| 6,326,019 B1 | 12/2001 | Tseng | |
| 6,335,349 B1 | 1/2002 | Muller | |
| 6,371,992 B1 | 4/2002 | Tanagho et al. | |
| 6,379,323 B1 | 4/2002 | Patterson | |
| 6,380,239 B1 | 4/2002 | Muller | |
| 6,387,367 B1 | 5/2002 | Davis-Sproul | |
| 6,395,754 B1 | 5/2002 | Muller | |
| 6,403,613 B1 | 6/2002 | Man | |
| 6,417,166 B2 | 7/2002 | Liu | |
| 6,428,802 B1 | 8/2002 | Atala | |
| 6,432,710 B1 | 8/2002 | Boss et al. | |

(Continued)

FOREIGN PATENT DOCUMENTS

DE 2631909 7/1976

(Continued)

OTHER PUBLICATIONS

U.S. Appl. No. 11/893,409, filed Aug. 15, 2007, Liu et al. U.S. Appl. No. 11/906,961, filed Oct. 3, 2007, Liu et al.
U.S. Appl. No. 11/973,902, filed Oct. 9, 2007, Bhatia et al.
Akle et al., 1981, "Immunogenicity of Human Amniotic Epithelial Cells After Transplantation Into Volunteers," The Lancet, 2: 1003-1005.
Allman, 2001, "Xenogenic Extracellular Matrix Grafts Elicit a TH2-Restricited Immune Response," Transplantation, 71(11):1631-1640.
Amenta et al., 1986, "The Extracellular Matrix is an Integrated Unit: Ultrastructural Localization of Collagen Types I, III, IV, V, VI, Fibronectin, and Laminin in Human Term Placenta," Coll. Relat. Res. 6(2):125-52.
Anderson et al., 2001, "Amniotic Membrane Transplantation After the Primary Surgical Management of Band Keratopathy," Cornea, 20(4):354-361.
Anderson et al., 2001, "Amniotic Membrane Transplantation for Partial Limbal Stem Cell Deficiency," British J. of Opthamology, 85:567-575.

(Continued)

*Primary Examiner* — Allison Ford
(74) *Attorney, Agent, or Firm* — Jones Day

(57) ABSTRACT

The present invention encompasses compositions, including solutions, gels, and pastes, manufactured from amniotic membrane, umbilical cord membrane, or both. The present invention also encompasses methods of making such compositions, and methods of using the compositions to treat conditions of the eye.

20 Claims, No Drawings

U.S. PATENT DOCUMENTS

| | | | |
|---|---|---|---|
| 6,432,712 | B1 | 8/2002 | Wolfinbarger, Jr. |
| 6,458,810 | B1 | 10/2002 | Muller |
| 6,476,052 | B1 | 11/2002 | Muller |
| 6,479,064 | B1 | 11/2002 | Atala |
| 6,555,554 | B2 | 4/2003 | Muller |
| 6,652,594 | B2 | 11/2003 | Francis et al. |
| 6,734,018 | B2 | 5/2004 | Wolfinbarger et al. |
| 6,753,181 | B1 | 6/2004 | Atala |
| 6,866,686 | B2 | 3/2005 | Ollerenshaw et al. |
| 6,962,814 | B2 | 11/2005 | Mitchell et al. |
| 7,045,148 | B2 | 5/2006 | Hariri |
| 7,091,353 | B2 | 8/2006 | Robarge |
| 2001/0037014 | A1 | 11/2001 | Liu |
| 2001/0038848 | A1 | 11/2001 | Donda et al. |
| 2002/0103542 | A1 | 8/2002 | Bilbo |
| 2002/0151974 | A1 | 10/2002 | Bonassar et al. |
| 2002/0197296 | A1 | 12/2002 | Gen |
| 2003/0032179 | A1 | 2/2003 | Hariri |
| 2003/0045552 | A1 | 3/2003 | Robarge |
| 2003/0143207 | A1 | 7/2003 | Livesey et al. |
| 2003/0180269 | A1 | 9/2003 | Hariri |
| 2003/0187515 | A1 | 10/2003 | Hariri |
| 2003/0235909 | A1 | 12/2003 | Hariri |
| 2004/0028660 | A1 | 2/2004 | Hariri |
| 2004/0048796 | A1 | 3/2004 | Hariri |
| 2005/0096351 | A1 | 5/2005 | Jaworsky |
| 2006/0084815 | A1 | 4/2006 | Muller |
| 2007/0020225 | A1 | 1/2007 | Abramson et al. |
| 2007/0021704 | A1 | 1/2007 | Hariri et al. |
| 2007/0021762 | A1 | 1/2007 | Liu et al. |
| 2007/0038298 | A1 | 2/2007 | Sulner et al. |
| 2007/0071740 | A1* | 3/2007 | Tseng et al. .......... 424/94.1 |
| 2007/0202189 | A1 | 8/2007 | Ahlfors |
| 2008/0044848 | A1 | 2/2008 | Heideran |

FOREIGN PATENT DOCUMENTS

| | | | |
|---|---|---|---|
| EP | 214853 | A2 | 3/1987 |
| EP | 0399782 | A2 | 11/1990 |
| EP | 526756 | A1 | 2/1993 |
| EP | 637452 | A1 | 2/1995 |
| EP | 734736 | A1 | 10/1996 |
| EP | 773033 | A1 | 5/1997 |
| EP | 781564 | A2 | 7/1997 |
| EP | 1031356 | A2 | 8/2000 |
| EP | 1103277 | | 5/2001 |
| FR | 2613620 | A1 | 10/1988 |
| GB | 2360789 | A | 10/2001 |
| JP | 62-268875 | | 11/1987 |
| JP | 5056987 | | 3/1993 |
| NL | 9101149 | | 2/1993 |
| SU | 1286211 | | 1/1987 |
| WO | WO 88/08305 | A1 | 11/1988 |
| WO | WO 95/07095 | A1 | 3/1995 |
| WO | WO 95/22301 | A1 | 8/1995 |
| WO | WO 96/13974 | A1 | 5/1996 |
| WO | WO 97/48405 | A1 | 12/1997 |
| WO | WO 98/03502 | A1 | 1/1998 |
| WO | WO 98/37903 | A1 | 9/1998 |
| WO | WO 98/54170 | A1 | 12/1998 |
| WO | WO 99/63051 | A1 | 12/1999 |
| WO | WO 99/65427 | A1 | 12/1999 |
| WO | WO 01/15750 | A1 | 3/2001 |
| WO | WO 01/66162 | A1 | 9/2001 |
| WO | WO 02/09647 | A2 | 2/2002 |
| WO | WO 02/59106 | A1 | 8/2002 |
| WO | WO 03/020297 | A2 | 3/2003 |
| WO | WO 03/087333 | A2 | 10/2003 |
| WO | WO 2004/026244 | A2 | 4/2004 |
| WO | WO 2006/094247 | A2 | 9/2006 |

OTHER PUBLICATIONS

Aplin et al., 1985, "The Extracellular Matrix of Human Amniotic Epithelium: Ultrastructure, Composition and Deposition," J. Cell Sci., 79:119-136.

Arora et al., 1994, "Controlled Comparison of Interceed and Amniotic Membrane Graft in the Prevention of Postoperative Adhesions in the Rabbit Uterine Horn Model," European Journal of Obstetrics Gynecology and Reproductive Biology, 55: 179-182.

Ashworth et al., 1986, "Vaginoplasty Using Amnion," Obstet. Gynecol., 67:443-446.

Atanassov et al., 1994, "Use of Amniotic Membranes As Biological Dressings in Contemporary Treatment of Burns," Ann. Medit. Burns Club, 7(4).

Atiyeh et al., 2002, "Management of Acute and Chronic Open Wounds: The Importance of Moist Environment in Optimal Wound Healing," Curr. Pharm. Biotechnol., 3:179-195.

Bachinger et al., 1990, "The Relationship of the Biophysical and Biochemical Characteristics of Type VII Collagen to the Function of Anchoring Fibrils," J. Biol. Chem., 265: 0095-10101.

Badawy et al., 1989, "Evaluation of Tissue Healing and Adhesion Formation After an Intraabdominal Amniotic Membrane Graft in the Rat," J. Reprod. Med., 34(3):198-202.

Badylak, 1999, "Endothelial Cell Adherence to Small Intestinal Submucosa: An Acellular Bioscaffold," Biomaterials, 20:2257-2263.

Badylak, 2002, "The Extracellular Matrix As a Scaffold for Tissue Reconstruction," Semin. Cell Dev. Biol., 13:377-383.

Bapat et al., 1974, "Preliminary Report on Acceleration of Wound Healing by Amnion Membrane Graft," Indian J. Med. Res., 62:1342-1346.

Bari et al., 2002, "Role of Human Foetal Membranes (Amniotic Membrane) in the Management of Burn Wounds," Annals of Burns and Fire Disasters, XV(4):1-8.

Barlas et al., 1992, "Human Amniotic Membrane As an Intestinal Patch for Neomucosal Growth in the Rabbit Model," J. Pediatr. Surg., 27(5):597-601.

Barton et al., 1997, "Amniotic Membrane Translplantation in Glaucoma Surgery," Investig. Opthalmology and Visual Science, Abstract Book, Part I: Annual Meeting, Ft. Lauderdale, Florida, May 11-16, 1997, 38(4):5473, Abstract 2194.

Bennett et al., 1980, "Treatment of Chronic Ulceration of the Legs With Human Amnion," Lancet, 1: 1153-1155.

Benque et al., 1997, "Combined Collagen Membrane and Hydroxyapatite/Collagen Chondroitin-Sulfate Spacer Placement in the Treatment of 2-Wall Intrabony Defects in Chronic Adult and Rapidly Progressive Periodontitis Patients," J. Clin. Periodontol., 24(8):550-556.

Black et al., 1994, "Comparative Study of Collagen and Expanded Polytetrafluoroethylene Membranes in the Treatment of Human Class II Furcation Defects," J. Periodontol., 65(6):598-604.

Bleggi-Torres et al., 1997, "Ultrastructural Study of the Neovagina Following the Utilization of Human Amniotic Membrane for Treatment of Congenital Absence of the Vagina," Brazilian Journal of Medical and Biological Research, 30: 861-864.

Blumenthal, 1993, "A Clinical Comparison of Collagen Membranes With E-PTFE Membranes in the Treatment of Human Mandibular Buccal Class II Furcation Defects," J. Periodontol., 64(10):925-933.

Boc et al., 1985, "Implications for the Use of Amnion and Chorion in Podiatric Medicine and Surgery," J. Foot Surg., 24(4):236-242.

Bose, 1979, "Burn Wound Dressing With Human Amniotic Membrane," Ann. R. Coll. Surg. Engl., 61:444-447.

Brito et al., 2003, "Effect of Topical Application of Fibronectin in Duodenal Wound Healing in Rats," Acta Cirurgica Brasileira, 18(2):97-101.

Bunyaratavej et al., 2001, "Collagen Membranes: A Review," J. Periodontol., 72(2):215-229.

Chang et al., 1994, "Frozen Preservation of Human Amnion and Its Use As a Burn Wound Dressing," Chang Gung Med. J., 17(4):316-324.

Chaplin et al., 1999, "Use of An Acellular Dermal Allograft for Dural Replacement: An Experimental Study," Neurosurgery, 45(2):320-327.

Chen et al., 1999, "Acellular Collagen Matrix As a Possible 'Off the Shelf' Biomaterial for Urethral Repair," Urology, 54(3):407-410.

Cheng et al., 1988, "Fibronectin Enhances Healing of Excised Wounds in Rats," Arch. Dermatol., 124:221-225.

Chung, et al., 1990, "Clinical Evaluation of a Biodegradable Collagen Membrane in Guided Tissue Regeneration," J. Periodontol., 61(12):732-736.

Chvapil et al., 1973, "Medical and Surgical Applications of Collagen," Int. Rev. Connect. Tissue Res., 6:1-61.

Colocho et al., 1974, "Human Amniotic Membrane As a Physiologic Wound Dressing," Arch. Surg., 109: 370-373.

Constantino et al., 2000, "Human Dural Replacement With Acellular Dermis: Clinical Results And A Review Of The Literature," Head & Neck, 22:765-771.

Davis et al., 1987, "Human Amnion Membrane Serves As a Substratum for Growing Axons In Vitro and In Vivo," Science, 236:1106-1109.

De Rotth, 1940, "Plastic Repair of Conjunctival Defects With Fetal Membranes," Arch. Of Opthalm., 23(3):522-525.

DeLustro et al., 1987, "Reaction to Injectable Collagen: Results in Animal Models and Clinical Use," Plast. Reconstr. Surg., 79(4):581-594.

DeLustro et al.,1990, "Immune Responses to Allogeneic and Xenogeneic Implants of Collagen and Collagen Derivatives," Clin. Orthop., 260:263-279.

DeMirkan et al., 2002, "The Use of Amniotic Membrane in Flexor Tendon Repair: An Experimental Model," Arch. Orthop. Trauma Surg., 122:396-399.

Dhall, 1984, "Amnion Graft for Treatment of Congenital Absence of the Vagina," Br. J. Obstet. Gynaecol., 91:279-282.

Dino et al., 1966, "Human Amnion: The Establishment of an Amnion Bank and Its Practical Application In Surgery," J. Philipp. Med. Assoc., 42(7):357-366.

Dong et al., 2002, "Some New Aspects in Biosensors," Reviews in Mol. Biotechnol., 82:303-323.

Dua et al., 1999, "Amniotic Membrane Transplantation," Br. J. Opthalmol., 83:748-752.

Eade, 1958, "The Relationship Between Granulation Tissue, Bacteria, and Skin Grafts in Burned Patients," Plast. Reconstr. Surg., 22(1):42-55.

Eckes et al., 2000, "Fibroblast-Matrix Interactions in Wound Healing and Fibrosis," Matrix Biol., 19:325-332.

Eldad et al., 1977, "Amniotic Membranes As a Biological Dressing," S. Afr. Med. J., 51(9):272-275.

Erdener et al., 1992, "Amniotic Membrane Wrapping: An Alternative Method to the Splenorrhaphy in the Injured Spleen," Eur. J. Pediatr. Surg., 2:26-28.

Faulk et al., 1980, "Human Amnion As an Adjunct in Wound Healing," Lancet, 1:1156-1158.

Flageul et al., 1994, "Le collagène injectable: bilan après 10 ans d'utilisation en complément de las chirurgie esthétique," Annales de Chirurgie Plastique Esthétique, 39(6):765-771.

Fletcher, 2000, "The Role of Collagen in Wound Healing," Prof. Nurse, 15(8):527-530.

Friess, 1998, "Collagen—Biomaterial for Drug Delivery," Eur. J. Pharm. Biopharm., 45(2):113-136.

Fujisato et al., 1999, "Cross-Linking of Amniotic Membranes," J. Biomater. Sci. Polym. Ed., 10:1171-1181.

Gamba et al., 2002, "Experimental Abdominal Wall Defect Repaired With Acellular Matrix," Pediatr. Surg. Int., 18:327-331.

Ganatra et al., 1996, "Method of Obtaining and Preparation of Fresh Human Amniotic Membrane for Clinical Use," J. Pak. Med. Assoc., 46(6):126-128.

Gebhardt et al., 1995, "Collagen As a Delivery System for Hydrophobic Drugs: Studies With Cyclosporine," J. Ocul. Pharmacol. Ther., 11(3):319-327.

Ghalambor et al., 2000, "The Amniotic Membrane: A Suitable Biological Dressing to Prevent Infection in Thermal Burns," Medical Journal of Islamic Academy of Sciences, 13(3):115-118.

Gharib et al., 1996, "Use of Amniotic Graft in the Repair of Gastroschisis," Pediatr. Surg. Int., 11:96-99.

Goepfert, 1991, "Collagen Injections," Arch. Otolaryngol. Head Neck Surg., 117(10):1189.

Gomes et al., 1996, "Effects of Human Amniotic Membrane on Dental Socket Wound Healing Process in Rats," Journal of Dental Research, 75(5):1114, Abstract 290.

Gomes et al., 2001, "Histologic Evaluation of the Osteoinductive Property of Autogenous Demineralized Dentin Matrix on Surgical Bone Defects in Rabbit Skulls Using Human Amniotic Membrane for Guided Bone Regeneration," International Journal of Oral & Maxillofacial Implants, 16(4):563-571.

Gomes et al., 2003, "Amniotic Membrane Transplantation for Partial and Total Limbal Stem Cell Deficiency Secondary to Chemical Burn," Opthamology, 110(3):466-473.

Graham, Med. Device Tech., 9(1):18-22 (1998).

Gris et al., 2002, "Amniotic Membrane Implantation As a Therapeutic Contact Lens for the Treatment of Epithelial Disorders," Cornea, 21(1):22-27.

Gris et al., 2002, "Histologic Findings after Amniotic Membrane Graft in the Human Cornea," Opthamology, 109(3):508-512.

Gruss et al., 1978, "Human Amniotic Membrane: A Versatile Wound Dressing," Can. Med. Assoc. J., 118:1237-1240 & 1245-1246.

Guler, et al., 1993, "A Comparative Histopathological Investigation of the Effect of Lyophilized Amniotic Membrane on Wound Healing As an Allograft Material in Rats," Journal of Islamic Academy of Sciences, 6(3), pp. 1-17.

Haberal et al., 1987, "The Use of Silver Nitrate-Incorporated Amniotic Membrane As a Temporary Dressing," Burns, 13(2):159-163.

Hammer et al., 1997, "Amnion Epithelial Cells, In Contrast to Trophoblast Cells, Express All Classical HLA Class I Molecules Together With HLA-G," Am. J. Reprod. Immunol., 37:161-171.

Heiligenhaus et al., 2001, "Improvement of HSV-1 Necrotizing Keratitis With Amniotic Membrane Transplantation," Investigative Opthamology and Visual Science, 42(9):1969-1974.

Hennink et al., 2002, "Novel Crosslinking Methods to Design Hydrogels," Advanced Drug Delivery Reviews, 54:13-36.

Herne et al., 2000, "New Facial Rejuvenation Techniques," Semin. Cutan. Med. Surg., 19(4):221-231.

Hodde, 2002, "Naturally Occurring Scaffolds for Soft Tissue Repair and Regeneration," Tissue Eng., 8(2):295-308.

Honovar et al., 2000, "Amniotic Membrane Transplantation for Ocular Surface Reconstruction in Stevens-Johnson Syndrome," Opthamology, 107(5):975-979.

John et al., 2002, "Amniotic Membrane in the Surgical Management of Acute Toxic Epidermal Necrolysis," Ophthalmology, 109(2):351-360.

John, 2003, "Human Amniotic Membrane Transplantation: Past, Present, and Future," Ophthalmol. Clin. North Am., 16:43-64.

Johnson, 1937, "Insulating Patches and Absorbable Sutures Made From Fetal Membranes," New England Journal of Medicine, 216(22):978-982.

Kakishita et al., 2000, "Human Amniotic Epithelial Cells Produce Dopamine and Survive After Implantation Into the Striatum of a Rat Model of Parkinson's Disease: A Potential Source of Donor for Transplantation Therapy," Exp. Neurol., 165(1):27-34.

Kane et al., 1996, "7.10 Burn Dressings," Biomaterials Science: An Introduction to Materials in Medicine, 360-370.

Kassouf et al., 2001, "Collagen Injection for Treatment of Urinary Incontinence in Children," J. Urol., 165(5):1666-1668.

Kershen et al., 2002, "Beyond Collagen: Injectable Therapies for the Treatment of Female Stress Urinary Incontinence in the New Millennium," Urol. Clin. North Am., 29(3):559-574.

Kim et al., 1995, "Transplantation of Preserved Human Amniotic Membrane for Surface Reconstruction in Severely Damaged Rabbit Corneas," Cornea, 14(5):473-484.

Kim et al., 2000, "Amniotic Membrane Patching Promotes Healing and Inhibits Proteinase Activity on Wound Healing Following Acute Corneal Alkali Burn," Experimental Eye Research, 70: 329-337.

Kirschbaum et al., 1963, "Use of Amnion in Extensive Burns," Third International Congress of Plastic Surgery, Washington, D.C., Oct. 13-18, 1963, Abstracts of Papers, p. 21, Abstract 33.

Klein, 2001, "Skin Filling. Collagen and Other Injectables of the Skin," Dermatol. Clin., 19(3):491-508.

Klen et al., 1976, "Influence of Ionizing Sterilization on the Permeability of Human Chorio-Amniotic, Dermo-Epidermal and Fascial Grafts," Res. Exp. Med., 167(1):15-21.

Koizumi et al., 2000, "Cultivation of Corneal Epithelial Cells on Intact and Denuded Human Amniotic Membrane," Investigative Opthamology and Visual Science, 41(9):2506-2513.

Koizumi et al., 2000, "Growth Factor mRNA and Protein in Preserved Human Amniotic Membrane," Current Eye Research, 20(3):173-177.

Kubo et al., 2001, "Immunogenicity of Human Amniotic Membrane in Experimental Xenotransplantation," Invest. Ophthalmol. Vis. Sci., 42(7):1539-1546.

Kucan et al., 1982, "Amniotic Membranes As Dressings Following Facial Dermabrasion," Ann. Plast. Surg., 8(6):523-527.

Lee et al., 1996, "Effect of Amniotic Fluid in Corneal Sensitivity and Nerve Regeneration After Excimer Laser Ablation," Cornea, 15(5):517-524.

Lee et al., 1997, "Amniotic Membrane Transplantation for Persistent Epithelial Defects With Ulceration," Am. J. Opthalm., 123(3):303-312.

Lee et al., 1998, "Mesothelial Cell Regeneration in Purified Human Amnion Membrane Grafts Implanted in Dog Pericardium," Tissue Engineering, 4(2):131-141.

Lee et al., 2001, "Biomedical Applications of Collagen," Int. J. Pharm., 221:1-22.

Lee et al., 2002, "Laminin Modified Infection-Preventing Collagen Membrane Containing Silver Sulfadiazine-Hyaluronan Microparticles," Artif. Organs, 26(6):521-528.

Lightner, 2002, "Review of the Available Urethral Bulking Agents," Curr. Opin. Urol., 12(4):333-338.

Mantovani et al., 2002, "Reconstructive Urethroplasty Using Porcine Acellular Matrix: Preliminary Results," 59$^{th}$ Convegno Associazione Urologi Lombardi—Milano, 26 Gennaio 2002, pp. 127-128 (Abstract in English).

Marzaro et al., 2002, "Autologous Satellite Cell Seeding Improves in Vivo Biocompatibility of Homologous Muscle Acellular Matrix Implants," International J. Mol. Med., 10:177-182.

Massee et al., 1962, "Use of Fetal Membranes As Replacement for Pelvic Peritoneum After Pelvic Exenteration In the Dog," Surg. Forum, 13:407-408.

Mattson et al., 1995, "Treatment of Intrabony Defects With Collagen Membrane Barriers," J. Periodontol., 66(7):635-645.

Mattson et al., 1999, "The Use of 2 Bioabsorbable Barrier Membranes in the Treatment of Interproximal Intrabony Periodontal Defects," J. Periodontol., 70(5):510-517.

McIndoe et al., 1938, "An Operation for the Cure of Congenital Absence of the Vagina," Journal of Obstetrics and Gynaecology, 490-494.

McPherson et al., 1986, "An Examination of the Biologic Response to Injectable Glutaraldehyde Cross Linked Collagen Implants," J. Biomed. Mater. Res., 20:93-107.

McPherson, 1992, "The Utility of Collagen-Based Vehicles in Delivery of Growth Factors for Hard and Soft Tissue Wound Repair," Clin. Mater., 9:225-234.

Meinert et al., 2001, "Proteoglycans and Hyaluronan in Human Fetal Membranes," Am. J. Obstet. Gynecol., 184(4): 679-685.

Meller et al., 2000, "Amniotic Membrane Transplantation for Symptomatic Conjunctivochalasis Refractory to Medical Treatments," Cornea, 19(6):796-803.

Meller et al., 2000, "Amniotic Membrane Transplantation for Acute Chemical or Thermal Burns," Opthamology, 107(5):980-989.

Merguerian et al., 2000, "Acellular Bladder Matrix Allografts in the Regeneration of Functional Bladders: Evaluation of Large-Segment (>24 cm$^2$) Substitution in a Porcine Model," BJU Intl., 85:894-898.

Mligiliche et al., 2002, "Extracellular Matrix of Human Amnion Manufactured Into Tubes As Conduits for Peripheral Nerve Regeneration," J. Biomed. Mater. Res., 63:591-600.

Morton et al., 1986, "Human Amnion in the Treatment of Vaginal Malformations," Br. J. Obstet. Gynaecol., 93:50-54.

Muralidharan et al., 1991, "A New Biological Membrane for Pericardial Closure," J. Biomed. Mater. Res., 25:1201-1209.

Murata et al., 1998, "Human Amniotic Membrane on Guided Bone Regeneration in Skull Defects," Journal of Dental Research, 77:840, Abstract 1668.

Nguyen et al., 2002, "Photopolymerizable Hydrogels for Tissue Engineering Applications," Biomaterials, 23(22):4307-4314.

Nisolle et al., 1992, "Vaginoplasty Using Amniotic Membranes in Cases of Vaginal Agenesis or After Vaginectomy," J. Gynecol. Surg., 8:25-30.

Oremus et al., 2002, "A Survey of Physician Efficacy Requirements to Plan Clinical Trials," Pharmacoepidemiology Drug Saf., 11(8):677-685.

Ozcan et al., 1997, "Combined Use of Root Conditioning, Fibrin-Fibronectin System and a Collagen Membrane to Treat a Localized Gingival Recession: A 10-Case Report," J. Marmara Univ. Dent. Fa., 2(4):588-598.

Ozeren et al., 1998, "The Effects of Human Amniotic Membrane and Fibrin Sealant in the Prevention of Postoperative Adhesion Formation in the Rabbit Ovary Model," Australian & New Zealand Journal of Obstetrics & Gynaecology, 38(2):207-209.

Pannek et al., 2001, "Particle Migration After Transurethral Injection of Carbon Coated Beads for Stress Urinary Incontinence," J. Urol., 166(4):1350-1353.

Parnigotto et al., 2000, "Experimental Defect in Rabbit Urethra Repaired with Acellular Aortic Matrix," Urol. Res., 28:46-51.

Patino et al., 2002, "Collagen as an Implantable Material in Medicine and Dentistry", J. Oral Implantol., 28(5):220-225.

Paul et al., 1992, "Use of a Collagen Barrier to Enhance Healing in Human Periodontal Furcation Defects," Int. J. Periodontics Restorative Dent., 12(2):123-131.

Paul et al., 2003, "Chemical Stabilisation of Collagen as a Biomimetic," The Scientific World, 3:138-155.

Peppas et al., 2000, "Hydrogels in Pharmaceutical Formulations," Eur. J. Pharm. Biopharm., 50(1):27-46.

Piazza et al., 1992, "Neovaginoplasty With McInndoe Technic and Use of Amniotic Membrane: Study With 15 Patients," Rev. Bras. Ginecol. Obstet., 14:224-226.

Pigeon, 1960, "Treatment of Second-Degree Burns with Amniotic Membranes," Can. Med. Assoc. J., 83:844-845.

Pires et al., 1999, "Amniotic Membrane Transplantation for Symptomatic Bullous Keratopathy," Archives of Opthamology, 117:1291-1297.

Power et al., 1995, "Analysis of the Acute Ophthalmic Manifestations of the Erythema Multiforme/Stevens-Johnson Syndrome/Toxic Epidermal Necrolysis Disease Spectrum," Ophthalmology, 102(11):1669-1676.

Prabhasawat et al., 1997, "Comparison of Conjunctival Autografts, Amniotic Membrane Grafts, And Primary Closure For Pterygium Excision," Ophthalmology, 104(6):974-985.

Prabhasawat et al., 1997, "Impression Cytology Study of Epithelial Phenotype of Ocular Surface Reconstructed by Preserved Human Amniotic Membrane," Arch. Ophthalmol., 115(11):1360-1367.

Prasad et al., 1986, "Use of Amnion for the Treatment of Stevens-Johnson Syndrome," J. Trauma, 26(10):945-946.

Prathiba et al., 2000, "Cutaneous Wound Healing: Significance of Proteoglycans in Scar Formation," Current Science, 78(6):1-5.

Quinby et al., 1982, "Clinical Trials of Amniotic Membranes in Burn Wound Care," Plast. Reconstr. Surg., 70:711-717.

Quteish et al., 1992, "The Use of Irradiated-Crosslinked Human Collagen Membrane in Guided Tissue Regeneration," J. Clin. Periodontol., 19(7):476-484.

Ramakrishnan et al., 1983, "Human Amniotic Membrane as a Temporary Biologic Dressing in Complicated Burns in a Developing Country," Journal of Burn Care & Rehabilitation, 4(3):202-204.

Rao et al., 1981, "Use of Dry Human and Bovine Amnion As a Biological Dressing," Arch. Surg., 116:891-896.

Rao, 1995, "Recent Developments of Collagen-Based Materials for Medical Applications and Drug Delivery Systems," J. Biomater. Sci. Polym. Ed., 7(7):623-645.

Reddy et al., 2000, "Regeneration of Functional Bladder Substitutes Using Large Segment Acellular Matrix Allografts in a Porcine Model," J. Urol., 164:936-941.

Rennekampff et al., 1994, "Evaluation of Amniotic Membrane As Adhesion Prophylaxis in a Novel Surgical Gastroschisis Model," J. Invest. Surg., 7:187-193.

Rigal-Sastourne et al., 2002, "Brulures Corneennes Et Metalloproteases: Influence Des Greffes De Membranes Amniotiques," J. Fr. Ophtalmol., 25:685-693.

Robson et al., 1973, "Amniotic Membranes as a Temporary Wound Dressing," Surg. Gynecol. Obstet., 136: 904-906.

Robson et al., 1973, "Quantitative Comparison of Biological Dressings," J. Surg. Res., 14: 431-434.

Robson et al., 1973, "The Effect of Human Amniotic Membranes on the Bacteria Population of Infected Rat Burns," Ann. Surg., 177(2):144-149.

Robson et al., 1974, "Clinical Experiences With Amniotic Membranes As a Temporary Biologic Dressing," Conn. Med., 38(9):449-451.

Sabella, 1913, "Use of Fetal Membranes in Skin Grafting," Med. Records NY, 83:478-480.

Sakuragawa et al., 1992, "Amniotic Tissue Transplantation: Clinical and Biochemical Evaluations for Some Lysosomal Storage Diseases," Brain Dev., 14(1):7-11.

Salisbury et al., 1980, "Comparison of the Bacterial Clearing Effects of Different Biologic Dressings on Granulating Wounds Following Thermal Injury," Plast. Reconstr. Surg, 66(4):596-598.

Sawhney, 1989, "Amniotic Membrane As a Biological Dressing in the Management of Burns," Burns, 15(5):339-342.

Schiff et al., 2003, "Towards a Sutureless Vasovasostomy: Use of Biomaterials and Surgical Sealants in a Rodent Vasovasostomy Model," Fertility and Sterility, 80(Suppl. 3): S92, Abstract O-240.

Schmedlen et al., 2002, "Photocrosslinkable Polyvinyl Alcohol Hydrogels that can be Modified with Cell Adhesion Peptides for use in Tissue Engineering," Biomaterials, 23:4325-4332.

Shieh et al., 1997,"Development and Clinical Evaluation of a Root Coverage Procedure Using A Collagen Barrier Membrane," J. Periodontol., 68(8):770-778.

Shimazaki et al., 1997, "Amniotic Membrane Transplantation for Ocular Surface Reconstruction in Patients With Chemical and Thermal Burns," Opthamology, 104(12):2068-2076.

Shimazaki et al., 2000, "Association of Preoperative Tear Function With Surgical Outcome in Severe Stevens-Johnson Syndrome," Ophthalmology, 107(8):1518-1523.

Shimazaki et al., 2002, "Transplantation of Human Limbal Epithelium Cultivated on Amniotic Membrane for the Treatment of Severe Ocular Surface Disorders," Opthamology, 109(7):1285-1290.

Shun et al., 1983, "Human Amnion in the Treatment of Chronic Ulceration of the Legs," Med. J. Aust., 2:279-283.

Silverton et al., 1979, "The Use of Amniotic Membrane in Acute Massive Full-Thickness Loss of the Abdominal Wall From Clostridial Myonecrosis," Ann. Plast. Surg., 3(6):558-566.

Singh et al., 2003, "Properties of Air Dried Radiation Processed Amniotic Membranes Under Different Storage Conditions," Cell and Tissue Banking, 4:95-100.

Skelhorne et al., 2002, "Hydrogel Adhesives for Wound-Care Applications," Med. Device Tech., 13(9):19-20 & 22-23.

Solomon et al., 2002, "Amniotic Membrane Grafts for Nontraumatic Corneal Perforations, Descemetoceles, and Deep Ulcers," Opthamology, 109(4):694-703.

Sorsby et al., 1946, "Amniotic Membrane Grafts in Caustic Burns of the Eye," Br. J. Opthamlol., 30:337-345.

Spira et al., 1994, "Human Amnion Collagen for Soft Tissue Augmentation—Biochemical Characterizations and Animal Observations," J. Biomed. Mat. Res., 28:91-96.

Stern, 1913, "The Grafting of Preserved Amniotic Membrane to Burned and Ulcerated Surfaces, Substituting Skin Grafts: A Preliminary Report," Journal of the American Medical Association, LX(13):973-974.

Subrahmanyam, 1995, "Amniotic Membrane As a Cover for Microskin Grafts," British Journal of Plastic Surgery, 48:477-478.

Szabo et al., 2000, "Evaluation of Seprafilm and Amniotic Membrane As Adhesion Prophylaxis in Mesh Repair of Abdominal Wall Hernia in Rats," European Surgical Research, 32:125-128.

Talmi et al., 1990, "Use of Human Amniotic Membrane As a Biologic Dressing," European Journal of Plastic Surgery, 13:160-162.

Talmi et al., 1991, "Antibacterial Properties of Human Amniotic Membranes," Placenta, 12:285-288.

Tancer et al., 1979, "Vaginal Epithelialization with Human Amnion," Obstet. Gynecol., 54(3):345-349.

Ti et al., 2001, "Amniotic Membrane Transplantation in Entropion Surgery," Opthamology, 108(7):1209-1217.

Trelford et al., 1972, "Amnion Autografts and Allografts As a Cover for Skin Defects in Sheep," J. Med., 3:81-87.

Trelford et al., 1972, "Considerations of the Amnion As an Autograft and As an Allograft in Sheep," J. Med., 3:231-241.

Trelford et al., 1973, "The Feasibility of Making an Artificial Vagina At the Time of Anterior Exenteration," Oncology, 28:398-401.

Trelford et al., 1975, "Amnion Autografts, Permanent Structure," J. Med., 6(3&4):243-247.

Trelford et al., 1973, "Amniotic Membrane As a Living Surgical Dressing in Human Patients," Oncology, 28:358-364.

Trelford et al., 1975, "Implanted Amniotic Membrane as an Autograft and as an Allograft," J. Med., 6(2):169-180.

Trelford-Sauder et al., 1977, "Replacement of the Peritoneum With Amnion Following Pelvic Exenteration," Surg. Gynecol. Obstet., 145:699-701.

Trelford et al., 1979, "The Amnion in Surgery, Past and Present," Am. J. Obstet. Gynecol., 134(7):833-845.

Troensagaard-Hansen et al., 1950, "Amniotic Grafts in Chronic Skin Ulceration," Lancet, 1:859-860.

Tseng et al., 1997, "Amniotic Membrane Transplantation for Conjunctival Surface Reconstruction," Am. J. Ophthalmol., 124(6):765-774.

Tseng et al., 1998, "Amniotic Membrane Transplantation With or Without Limbal Allografts for Corneal Sufrace Reconstruction in Patients With Limabal Stem Cell Deficiency," Archives of Opthamology, 116:431-441.

Tseng, 2001, "Amniotic Membrane Transplantation for Ocular Surface Reconstruction," Biosci. Rep., 21(4):481-489.

Tsubota et al., 1996, "Surgical Reconstruction of the Ocular Surface in Advanced Ocular Cicatricial Pemphigoid and Stevens-Johnson Syndrome," Am. J. Ophthalmol., 122(1):38-52.

Ueta et al., 2002, "Immunosuppressive Properties of Human Amniotic Membrane for Mixed Lymphocyte Reaction," Clinical and Experimental Immunology, 129: 464-470.

Voytik-Harbin et al., 1997, "Identification of Extractable Growth Factors From Small Intestinal Submucosa," J. Cell Biochem., 67:478-491.

Wagshall et al., 2002, "Acellular Dermal Matrix Allograft in the Treatment of Muciogingival Defects in Children: Illustrative Case Report," J. Dentistry for Children, 79:39-43.

Walker et al., 1977, "Use of Fresh Amnion As a Burn Dressing," J. Pediatr. Surg., 12(3):391-395.

Wallace et al., 1988, "Injectable Collagen for Tissue Augmentation," Collagen vol. III Biotechnology, Chapter 5, 117-144.

Wang et al., 1994, "Evaluation of an Absorbable Collagen Membrane in Treating Class II Furcation Defects," J. Periodontol., 65(11):1029-1036.

Wang et al., 1997, "Corneal Haze Is Reduced by Amniotic Membrane Matrix in Excimer Laser Photoablation in Rabbits," Investig. Opthalmology and Visual Science Abstract Book Part I, Annual Meeting, Ft. Lauderdale, Florida May 11-16, 1997, 38(4):S405, Abstract 1908-B701.

Wang et al., 1999, "Clinical Comparison of Two Techniques for Treatment of Gingival Recession," J. Dent. Res., 78 (IADR Abstracts):119, Abstract 106.

Ward et al., 1984, "The Long Term Results of the Use of Human Amnion in the Treatment of Leg Ulcers," British Journal of Plastic Surgery, 37: 191-193.

Ward et al., 1989, "The Healing of Chronic Venous Leg Ulcers With Prepared Human Amnion," Br. J. Plast. Surg., 42:463-467.

Wefer et al., 2002, "Homologous Acellular Matrix Graft for Vaginal Repair in Rats: A Pilot Study for a New Reconstructive Approach," World J. Urol., 20:260-263.

Yannas et al., 1980, "Design of an Artificial Skin: Control of Chemical Composition," J. of Biomed. Mat. Res., 14:107-132.

Yarborough et al., 1991, "Collagen Injections. A Case Study in the Erosion of the Medical Profession," Arch. Otolaryngol. Head Neck Surg., 117(1):270-272.

Young et al., 1991, "The Use of an Amniotic Membrane Graft to Prevent Postoperative Adhesions," Fertil. Steril., 55(3): 624-628.

Yukna et al., 1996, "Multi-Center Evaluation of Bioabsorbable Collagen Membrane for Guided Tissue Regeneration in Human Class II Furcations," J. Periodontol., 67(7):650-657.

Zahedi et al., 1998, "A 2-Year Clinical Evaluation of a Diphenylphosphorylazide-Cross-Linked Collagen Membrane for the Treatment of Buccal Gingival Recession," J. Periodontol., 69(9):975-981.

Zeeman et al., 1999, "Crosslinking and Modification of Dermal Sheep Collagen Using 1,4-butanediol diglycidyl ether," J. Biomed. Mater. Res., 46:424-433.

Zimmermann et al., 2000, "Hydrogel-Based Non-Autologous Cell and Tissue Therapy," BioTechniques, 29(3):564-572, 574, 576-581.

International Search Report and Written Opinion for PCT/US2007/021491, dated Jun. 4, 2008.

* cited by examiner

PLACENTAL TISSUE COMPOSITIONS

1. PRIOR RELATED APPLICATION

This application claims the benefit under 35 U.S.C. §119 (e) of U.S. Provisional Patent Application No. 60/849,521, filed Oct. 4, 2006, which is incorporated herein by reference in its entirety.

2. FIELD OF THE INVENTION

The present invention generally relates to compositions, e.g., solutions, gels or pastes, made from placenta, umbilical cord, or both, or tissues from placenta, umbilical cord, or both.

3. BACKGROUND OF THE INVENTION

The repair or treatment of various body tissues, such as skin, organs, and the like, has been accomplished using collagen compositions, including tissue membranes comprising collagen, e.g., amniotic membrane, pericardium, dura mater, and the like. A need exists, however, for additional, more versatile compositions that can be used in medical applications in addition to, or in place of, membranes.

4. SUMMARY OF THE INVENTION

The present invention provides compositions comprising aqueous-soluble components, including acid- or base-soluble components, of placental tissue and/or umbilical cord tissue, e.g., amniotic membrane and umbilical cord membrane, including umbilical cord membrane in combination with Wharton's jelly, and methods of making and using the same.

In one embodiment, the invention provides a composition comprising placental tissue components or umbilical cord components that are soluble in aqueous solution at neutral pH, and are substantially lacking placental tissue components or umbilical cord components that are insoluble in aqueous solution at neutral pH. In another embodiment, the invention provides a composition comprising placental tissue components or umbilical cord components that are soluble in aqueous solution at neutral pH, and placental tissue components or umbilical cord components that are insoluble in aqueous solution at neutral pH. In another embodiment, the invention provides a composition comprising placental tissue components or umbilical cord components that are soluble in aqueous solution at acidic and neutral pH, or basic and neutral pH, and are substantially lacking placental tissue components or umbilical cord components that are insoluble in aqueous solution at acidic and neutral pH or basic and neutral pH. In another embodiment, the invention provides a composition comprising placental tissue components or umbilical cord components that are soluble in aqueous solution at acidic and neutral pH, or basic and neutral pH, and placental tissue components or umbilical cord components that are insoluble in aqueous solution at acidic and neutral pH or basic and neutral pH. In another embodiment, said placental components or said umbilical cord components substantially lack acid- or base-insoluble amniotic membrane components.

In a specific embodiment of the above compositions, said placental tissue is amniotic membrane (AM). In another embodiment, said compositions are derived from a mixture of amniotic membrane and umbilical cord tissue components.

In other specific embodiments, the composition is a liquid, gel, paste or slurry. In other specific embodiments, the composition is a cream or ointment.

In certain specific embodiments, the composition comprises at least, about, or at most $1\times10^{-9}$, $5\times10^{-9}$, $1\times10^{-8}$, $5\times10^{-8}$, $1\times10^{-7}$, $5\times10^{-7}$, $1\times10^{-6}$, $5\times10^{-6}$, $1\times10^{-5}$, $5\times10^{-5}$, $10^{-4}$, $5\times10^{-4}$, $1\times10^{-3}$, $5\times10^{-3}$, $1\times10^{-2}$, $5\times10^{-2}$, or $1\times10^{-1}$ grams of placental tissue components or umbilical cord tissue components, or a particular tissue component, or a particular type of tissue component, per gram of composition or per milliliter of composition. In a specific embodiment, the tissue component is a cytokine or growth factor.

In other specific embodiments, the composition comprises at least or at most 1%, 5%, 10%, 20%, or 50% placental tissue components or umbilical cord tissue components by weight. In another specific embodiment, the composition is a lyophilized composition. In a specific embodiment, the composition comprises less than about 20% water by weight.

In another specific embodiment, the composition comprises an ophthalmologically-acceptable liquid, e.g., an isotonic buffer liquid. In a specific embodiment, the composition comprises less than 1% solids by weight. In a more specific embodiment, said liquid comprises saline solution, glycerin, hypromellose, or polyethylene glycol. In another more specific embodiment, said liquid comprises saline solution, glycerin, hypromellose, and polyethylene glycol. In another specific embodiment, the composition comprises an ophthalmologically-acceptable lubricant. In a more specific embodiment, said lubricant is hydrophobic. In another more specific embodiment, said lubricant is hydrophilic. In another more specific embodiment, said composition comprises one or more of an anti-inflammatory compound, an analgesic, an anesthetic or an immune-suppressing agent.

The invention further provides a bandage contact lens, wherein the contact lens comprises a solution, gel or paste of the invention.

The invention further provides a composition of the invention that comprises riboflavin as a crosslinking agent. The composition preferably comprises collagen. In a specific embodiment, the composition of the invention comprises collagen that is crosslinked by riboflavin. In another specific example, the invention provides a bandage contact lens, comprising collagen, wherein the collagen is crosslinked by riboflavin. Such a bandage contact lens can be made, e.g., by immersing the contact lens in a solution of the invention, wherein the solution comprises riboflavin, and exposing the lens to ultraviolet light (UVA) for a time sufficient for the UVA to crosslink a plurality of the collagens in the lens.

The invention further provides methods of preparing the compositions of the invention. In one embodiment, the invention provides a method of preparing a composition, comprising: (a) in either order: (i) contacting a placental tissue, umbilical cord tissue, or portion of either, with an acidic or basic solution; (ii) disrupting the placental tissue, umbilical cord tissue or portion thereof in said solution to form a suspension; (b) bringing the suspension to neutral pH; and (c) removing particulate matter within said suspension to form the composition.

In another embodiment, the invention provides a method of preparing a composition, comprising: (a) disrupting umbilical cord tissue in a pH-neutral aqueous solution to form a suspension; and (b) removing umbilical cord tissue components insoluble in said suspension to form the composition.

In a specific embodiment of these methods, said acidic solution is an acetic acid solution. In a more specific embodiment, said acidic solution is between about pH 4.5 and about pH 6. In another specific embodiment of the methods, said basic solution is a sodium hydroxide solution. In a more specific embodiment, said basic solution is between about pH 8 and about pH 9.5. In another specific embodiment, said disrupting is performed at a temperature of between about the freezing point of said solution to about 10° C. In other specific embodiments, the method comprises adjusting the water content of the solution to at most about 99%, 95%, 90%, 75%, 50% or 10% by weight. In another specific embodiment, the method comprises decellularizing said placental tissue or said umbilical cord tissue prior to said disruption. In a specific embodiment of the method, said placental tissue is amniotic membrane. In another specific embodiment of the method, said umbilical cord tissue is umbilical cord membrane in combination with Wharton's jelly.

The invention further comprises methods of using the compositions of the invention. In one embodiment, for example, the invention provides a method of treating a condition of an eye comprising contacting a tissue of said eye having or affected by said condition with a composition of the invention, preferably a solution of the invention. In specific embodiments, said ocular condition is irritation, dry eye, blepharitis, symblepharon, red eye, inflammation of a tissue of an eye or injury of a tissue of an eye. In a more specific embodiment, said injury is an injury caused by or related to refractive surgery. In an even more specific embodiment, said refractive surgery is photorefractive keratectomy (PRK), laser-assisted sub-epithelial keratectomy (LASEK), laser-assisted in situ keratomileusis (LASIK), automated lamellar keratoplasty (ALK), laser thermal keratoplasty (LTK), or conductive keratoplasty (CK). In another specific embodiment, the invention provides a method of treating a injury, wound or discontinuity in a tissue of an individual, comprising contacting said injury, wound or discontinuity with a compound of the invention. In a specific embodiment, said contacting is performed after said wound, injury or discontinuity is closed. In specific embodiments, said injury, wound or discontinuity is a laceration, scrape, thermal or chemical burn, incision, puncture, wound caused by a projectile.

The invention further provides a method of preparing a contact lens prior to placement on an eye, comprising contacting said contact lens with the composition of the invention. In a specific embodiment, said contact lens is a bandage contact lens.

As used herein, the term "components," as in "amniotic membrane components," means any part of a placenta or umbilical cord that is not an intact organ or tissue of the organ; the term can include, e.g., placental or umbilical cord biomolecules, or placental material in suspension produced by homogenization or disruption of placental or umbilical cord.

As used herein, "tissue" means an anatomically-distinct part or division of an organ. For example, "placental tissue" comprises, e.g., amniotic membrane or chorion.

As used herein, "treat" or "treatment" refers to the use of a composition of the invention on or in, e.g., a burn, injury, wound, or discontinuity in a tissue of an individual, e.g., contacting the injury, wound or discontinuity with the composition, such that at least one aspect of the injury, wound, or discontinuity is measurably improved compared to that of an individual on which the composition is not used. An "aspect of the injury, wound, or discontinuity" includes aspects such as, for example, the degree of inflammation, leakage of fluid, perceived discomfort, irritation, degree of tissue repair, degree of re-epithelialization, and the like. The term also encompasses the use of a composition of the invention to, e.g., improve the appearance of normal skin.

5. DETAILED DESCRIPTION OF THE INVENTION

The present invention provides for the use of placental tissue, e.g., whole placenta, amniotic membrane, chorion, and the like, and/or umbilical cord tissue, e.g., whole umbilical cord, umbilical cord membrane, Wharton's jelly, umbilical vessels, and the like, or a combination of any of the foregoing, to produce useful compositions such as solutions, gels or pastes. In one embodiment, the compositions are useful in treating a disease, disorder or condition of the eye. In another preferred embodiment, the compositions can be used as wound-healing agents.

5.1. Amniotic Membrane and/or Umbilical Cord Membrane Compositions and Methods of Making the Same

5.1.1. Obtaining Umbilical Cord and Amniotic Tissue

Placental tissue, e.g., amniotic membrane, to be used in making the compositions of the invention, can be obtained as follows. In a preferred embodiment, the placenta for use in the methods of the invention is taken as soon as possible after delivery of the newborn. The placenta may be used immediately, or may be stored for 2-5 days from the time of delivery prior to any further treatment. The placenta is typically exsanguinated, that is, drained of the cord blood remaining after birth. Preferably, the expectant mother is screened prior to the time of birth, using standard techniques known to one skilled in the art, for communicable diseases including but not limited to, HIV, HBV, HCV, HTLV, syphilis, CMV, and other pathogens known to contaminate placental tissue.

One exemplary method of obtaining placental tissue comprises the following steps. First, the umbilical cord is separated from the placental disc; optionally, the amniotic membrane is separated from the chorionic membrane. Following separation of the amniotic membrane from the chorionic membrane and placental disc, the umbilical cord stump is cut, e.g., with scissors, and detached from the placental disc. The placental tissue, e.g., amniotic membrane may then be stored in a sterile, preferably buffered, saline solution, such as 0.9% sterile NaCl solution. The placental tissue, e.g., amniotic membrane can stored by refrigeration, at a temperature of at least 2° C. in preparation for making a solution, gel or paste of the invention.

The umbilical cord can be collected as part of the collection of placental tissue, e.g., amniotic membrane. The umbilical cord is separated from the placenta as soon as possible after delivery of the newborn, and is typically massaged to remove umbilical cord blood. Optionally, the umbilical cord is sectioned into pieces of about 10 cm to about 15 cm in length. The umbilical cord or umbilical cord sections can then be stored for up to about 72 hours in a sterile, preferably buffered, saline solution, such as 0.9% sterile NaCl solution. Preferably, the umbilical cord is stored under refrigeration, at a temperature of about 1° C. to about 5° C. At this time, the umbilical cord is preferably slit or cut longitudinally using, e.g., a scalpel and forceps, grooved director, or the like, allowing removal of the Wharton's jelly, and/or removal of one or more of the umbilical cord vessels, e.g., with a forceps. Preferably, the vessels are removed, and the Wharton's jelly is retained. The umbilical cord membrane can also be processed further without cutting and opening the membrane. An umbilical cord vessel, for example, can be removed from the cord by grasping the vessels with a forceps and gently pulling and massaging until the vessel is removed, leaving the umbilical cord membrane as an intact tube. In one embodiment of deveining, the umbilical vein of a fresh (less than 48 hours after delivery) umbilical cord is canalized using the blunt probe of a vein stripper. The blunt probe is replaced with a small bullet probe, and the vein is tied to the probe with thread. The stripper is then removed, and the process is repeated with the umbilical arteries.

In preferred embodiments, the placental tissue or umbilical tissue used to make the composition of the invention, e.g., suspension, solution, slurry gel or paste, retains the tissue's native cells. In other embodiments, the placental tissue or umbilical cord tissue can be substantially decellularized; that is, substantially all cellular material and cellular debris (e.g., all visible cellular material and cellular debris) can removed from the tissue prior to production of a solution, gel or paste of the invention. Any decellularizing process known to one skilled in the art may be used, e.g., decellularization methods disclosed in U.S. Application Publication No. 2002/0160510. Preferably the process used for decellularizing the umbilical cord or umbilical cord membrane does not disrupt the native conformation of the proteins making up the biomaterial. In one embodiment, placental or umbilical cord tissue to be used in making a composition of the invention can be decellularized by contacting, e.g., placing the tissue in, a solution of about 0.5% to about 2.0% deoxycholic acid for a period of 1 hour to about 20 days, preferably about 1 hour to about 10 days, optionally in combination with physical scraping to remove cellular material. "Substantially decellularized," as used herein, means removal of at least 90% of the cells, more preferably at least 95% of the cells, and most preferably at least 99% of the cells associated with the umbilical cord membrane. Decellularization can leave cellular material on the membrane; for example, decellularization can leave nuclear material detectable by 4',6-diamidino-2-phenylindole (DAPI).

5.1.2. Solutions, Gels and Pastes

The present invention provides compositions, such as, e.g., solutions, suspensions, gels and pastes, that are made from placental tissue or umbilical cord tissue, e.g., amniotic membrane, chorion, amnion chorion, umbilical cord membrane, umbilical cord membrane combined with Wharton's jelly, etc. The present invention further provides methods of making these compositions.

5.1.2.1. Compositions Comprising Placental Tissue Components and/or Umbilical Cord Components Soluble at Neutral pH The invention generally provides compositions made from umbilical cord tissue or a combination of umbilical cord tissue and placental tissue. In one embodiment, the invention provides a suspension of umbilical cord tissue, or of umbilical cord tissue and placental tissue. Such suspensions comprise umbilical cord tissue, or placental and umbilical cord tissue, that has been disrupted, e.g., homogenized in aqueous solution such that the suspension comprises tissue components that are soluble in aqueous solution at neutral pH (i.e., about pH 7.0 to about pH 7.4), and components that are insoluble in aqueous solution at neutral pH. Such suspensions can be made by any method known to those of skill in the art. In one embodiment, the placental tissue or umbilical cord tissue is placed in a volume of a solution and disrupted, e.g., homogenized, to produce a suspension In certain embodiments, the suspension comprises components, both soluble and insoluble in aqueous solution, of a part of, or the whole of, only placental tissue, e.g., components of a whole placenta, or components only of parts of a placenta, such as amniotic membrane, chorion, or combination of amniotic membrane and chorion, and the like. In another embodiment, the suspension can comprise components of a part of, or the whole of, only umbilical cord tissue, e.g., components of a whole umbilical cord, or components only of umbilical cord membrane, Wharton's jelly, umbilical vessels, or a combination thereof. In one embodiment, the suspension comprises components from an amniotic membrane. In another embodiment, the suspension comprises components from an umbilical cord membrane in combination with Wharton's jelly. The invention also comprises suspensions that are combinations of the foregoing, as well, for example, a combination of amniotic membrane and umbilical cord membrane components.

In one embodiment, the suspension of the invention comprises umbilical cord tissue components, or a combination of umbilical cord tissue components and placenta tissue components, wherein said suspension is made by a process comprising (1) contacting umbilical cord tissue, or umbilical cord and placental tissue, with a solution at neutral pH, and (2) disrupting said tissue in said solution to form a suspension.

In other embodiments, the invention provides a suspension that comprises components of umbilical cord tissue, or both placental tissue and umbilical cord tissue, that are soluble in aqueous solution at neutral pH, and components thereof that are insoluble in aqueous solution at neutral pH. For example, the suspension can comprise components of a whole placenta and a whole umbilical cord; components of a whole placenta and a portion of an umbilical cord (e.g., membrane only, membrane and Wharton's jelly only, Wharton's jelly only, umbilical vessels only, etc.); components of a whole umbilical cord and a portion of a placenta (e.g., components of amniotic membrane only, chorion only, amnion and chorion, etc.). In another embodiment, the suspension can also comprise components of a portion of a placenta and a portion of an umbilical cord, e.g., components of an amniotic membrane and components of an umbilical cord membrane; components of an amniotic membrane and components of an umbilical cord membrane and Wharton's jelly, components of an amniotic membrane and components of Wharton's jelly, and the like, in any combination.

In embodiments in which the suspension comprises components of both placental tissue and umbilical cord tissue, the components, either or both of components soluble or insoluble in aqueous solution at neutral pH, can be present in the suspension in any ratio. Thus, the suspension can comprise predominantly (i.e., greater than 50%) placental tissue components relative to umbilical cord tissue, or predominantly umbilical cord tissue components relative to placental tissue. In other embodiments, the suspension comprises about 1%, 2%, 3%, 4%, 5%, 10%, 20%, 30%, 40%, 50%, 60%, 70%, 80%, 90%, 95%, 96%, 97%, 98%, or about 99% placental components or umbilical cord components out of total placental and umbilical cord components in the suspension.

In another embodiment, the composition provided by the present invention is a solution comprising components of placental tissue and/or umbilical cord tissue that are soluble in aqueous solution at neutral pH (i.e., about pH 7.0 to about pH 7.4), but substantially lacking components of placental tissue and/or umbilical cord tissue that are insoluble in aqueous solution at neutral pH and removable by, e.g., centrifugation and/or filtration. For example, such solutions, according to the invention, can comprise about 0.5%, 0.1%, 0.05% or 0.01% or less placental tissue components and/or umbilical cord tissue components, insoluble in aqueous solution at neutral pH (i.e., about pH 7.0 to about pH 7.4), by weight. Thus, in one embodiment, the invention provides a solution that comprises part or all of the fraction of placental tissue and/or umbilical cord tissue components that are soluble in pH-neutral aqueous solution and lacks components of placental tissue and/or umbilical cord tissue that are insoluble in aqueous solution at neutral pH.

In one embodiment, the solution of the invention comprises umbilical cord tissue components, or a combination of umbilical cord tissue components and placenta tissue components, wherein said solution is made by a process comprising (1) contacting umbilical cord tissue, or umbilical cord and placental tissue, with a solution at neutral pH, (2) disrupting said tissue in said solution to form a suspension; and (3) removing tissue components that are insoluble at neutral pH from said suspension.

In certain embodiments, the solution comprises components of a part of, or the whole of, only placental tissue, wherein the components are soluble in pH-neutral aqueous solution, e.g., components only of a whole placenta, or components only of parts of a placenta, such as amniotic membrane, chorion, or combination of amniotic membrane and chorion, and the like. Similarly, the solution can comprise components of a part of, or the whole of, only umbilical cord tissue, that are soluble in pH-neutral aqueous solution, e.g., components of only a whole umbilical cord, or components only of umbilical cord membrane, Wharton's jelly, umbilical vessels, or a combination thereof. In one embodiment, the solution comprises components from an amniotic membrane that are soluble in pH-neutral aqueous solution. In another embodiment, the solution comprises components from an umbilical cord membrane in combination with Wharton's jelly that are soluble in pH-neutral aqueous solution. The invention comprises solutions that are combinations of the foregoing, as well.

In certain other embodiments, the solution comprises components of placental tissue and umbilical cord tissue that are soluble in pH-neutral aqueous solution. For example, the solution can comprise components, soluble in pH-neutral aqueous solution, of a whole placenta and a whole umbilical cord; components of a whole placenta and a portion of an umbilical cord (e.g., membrane only, membrane and Wharton's jelly only, Wharton's jelly only, umbilical vessels only, etc.); components of a whole umbilical cord and a portion of a placenta (e.g., components of amniotic membrane only, chorion only, amnion and chorion, etc.). In another embodiment, the solution can also comprise components, soluble in pH-neutral aqueous solution, of a portion of a placenta and a portion of an umbilical cord, e.g., components of an amniotic membrane and components of an umbilical cord membrane; components of an amniotic membrane and components of an umbilical cord membrane and Wharton's jelly, components of an amniotic membrane and components of Wharton's jelly, and the like, in any combination.

In embodiments in which the solution comprises components of both placental tissue and umbilical cord tissue, the components can be present in the solution in any ratio. Thus, the solution can comprise predominantly (i.e., greater than 50%) placental tissue components soluble in aqueous solution relative to umbilical cord tissue soluble in aqueous solution, or predominantly umbilical cord tissue components soluble in aqueous solution at neutral pH relative to placental tissue soluble in aqueous solution at neutral pH. In other embodiments, the solution can comprise about 1%, 2%, 3%, 4%, 5%, 10%, 20%, 30%, 40%, 50%, 60%, 70%, 80%, 90%, 95%, 96%, 97%, 98%, or about 99% placental components or umbilical cord components, soluble in aqueous solution at neutral pH, out of a total of placental and umbilical cord components soluble in aqueous solution at neutral pH.

In various embodiments, the solutions comprise about, no more than, 0.1%, 0.2%, 0.3%, 0.4%, 0.5%, 0.6%, 0.7%, 0.8%, 0.9%, 1.0%, 1.2%, 1.4%, 1.6%, 1.8%, 2%, 3%, 4%, 5%, 6%, 7%, 8%, 9% or 10% placental tissue components, umbilical cord components, or a combination thereof, by weight. In other embodiments, the solutions comprise at least, about, or at most $1\times10^{-9}$, $5\times10^{-9}$, $1\times10^{-8}$, $5\times10^{-8}$, $1\times10^{-7}$, $5\times10^{-7}$, $1\times10^{-6}$, $5\times10^{-6}$, $1\times10^{-5}$, $5\times10^{-5}$, $10^{-4}$, $5\times10^{-4}$, $1\times10^{-3}$, $5\times10^{-3}$, $1\times10^{-2}$, $5\times10^{-2}$, or $1\times10^{-1}$ grams of tissue components, or a particular tissue component, or particular type of tissue component, per gram of composition or per milliliter of composition. Such tissue components can be, e.g., soluble proteins such as, e.g., cytokines or growth factors.

In another embodiment, the invention provides compositions comprising components of placental tissue and/or of umbilical cord tissue, soluble in aqueous solution at neutral pH, wherein the composition is a slurry, paste or gel. Generally, the components of placental tissue and/or of umbilical cord tissue, soluble in aqueous solution at neutral pH in the slurry or paste are the components, soluble in aqueous solution at neutral pH, of the solutions and suspensions described above. In various embodiments, such compositions are about 99%, 98%, 97%, 96%, 96%, 90%, 85%, 80%, 75%, 70%, 65%, 60%, 55%, 50%, 45%, 40%, 35%, 30%, 25%, 20%, 15%, 10%, 9%, 8%, 7%, 6%, 5%, 4%, 3%, 2% or about 1%, or are at least about, or at most about, 99.5%, 99%, 98%, 97%, 96%, 96%, 90%, 85%, 80%, 75%, 70%, 65%, 60%, 55%, 50%, 45%, 40%, 35%, 30%, 25%, 20%, 15%, 10%, 9%, 8%, 7%, 6%, 5%, 4%, 3%, 2% or about 1% water by weight. Similarly, in other embodiments, such compositions are about 99.5%, 99%, 98%, 97%, 96%, 96%, 90%, 85%, 80%, 75%, 70%, 65%, 60%, 55%, 50%, 45%, 40%, 35%, 30%, 25%, 20%, 15%, 10%, 9%, 8%, 7%, 6%, 5%, 4%, 3%, 2% or about 1%, or is at least about, or at most about, 99.5%, 99%, 98%, 97%, 96%, 96%, 90%, 85%, 80%, 75%, 70%, 65%, 60%, 55%, 50%, 45%, 40%, 35%, 30%, 25%, 20%, 15%, 10%, 9%, 8%, 7%, 6%, 5%, 4%, 3%, 2% or about 1% tissue components, insoluble at neutral pH, by weight.

The invention further provides combinations of the above compositions. For example, a slurry, gel or paste can be combined with a suspension; a solution of the invention can be combined with a suspension; a solution of the composition can be combined with a slurry, paste, gel etc. of the invention. In such embodiments, the respective compositions can each be from the same individual, or can be from different individuals. For example, in a combination of a solution of the invention and a paste of the invention, the solution can be from placental tissue and/or umbilical cord tissue of a single individual or from a plurality of individuals, and the paste can be placental tissue and/or umbilical cord tissue of a single individual or from a plurality of individuals. In a preferred embodiment, the compositions are from a single individual. Other combinations of suspensions, solutions, slurries and/or pastes can be from single individuals or pluralities of individuals in like fashion.

5.1.2.2. Compositions Comprising Placental Tissue Components and/or Umbilical Cord Components Soluble at Acidic or Basic pH In another embodiment, the invention provides compositions comprising components of placental tissue and/or umbilical cord tissue that are soluble at neutral pH and are soluble in an acidic or basic aqueous solution, e.g., an aqueous solution having a pH of about pH 6 or less, or a pH of about pH 8 or more. In various embodiments, the acidic solution in which the components are soluble is between about pH 4 and about pH 6; about pH 6.0, about pH 5.3, about pH 5.0, about pH 4.3, about pH 4.0, about pH 3.3 or about pH 3.0. In various other embodiment, the basic solution in which the components are soluble is between about pH 8 and about pH 11; about pH 8.0, about pH 8.3, about pH 9.0, about pH 9.3, about pH 10, about pH 10.3, or about pH 11.

In one embodiment, the composition of the invention comprising such placental tissue and/or umbilical cord tissue components, soluble in an neutral and acidic or neutral and basic aqueous solution, is a suspension of placental tissue and/or umbilical cord tissue. Such a suspension comprises, e.g., placental tissue and/or umbilical cord tissue that has been disrupted or homogenized in aqueous solution such that the suspension comprises placental tissue and/or umbilical cord tissue components that are soluble in neutral and acidic or neutral basic aqueous solution, and components that are insoluble in aqueous neutral and acidic or neutral and basic solution.

In one embodiment, the invention provides a composition comprising placental and/or umbilical cord tissue components that are soluble neutral and acidic or neutral basic aqueous solution, and components that are insoluble in aqueous neutral and acidic or neutral and basic solution, wherein said composition is made by a process comprising the steps of disrupting placental and/or umbilical cord tissue components in aqueous solution at neutral pH to form a suspension, acidifying or basifying the suspension, and then bringing said composition to neutral pH.

In another embodiment, the composition comprises placental and/or umbilical cord tissue components that are soluble in acidic and neutral, or basic and neutral, aqueous solution, and components that are insoluble in neutral and acidic, or neutral and basic, aqueous solution, is made by a process comprising the steps of disrupting placental and/or umbilical cord tissue components in acidic or basic aqueous solution to form a suspension, and bringing said suspension to a neutral pH.

In certain embodiments, the suspension comprises components, both soluble and insoluble in acidic or basic aqueous solution, of a part of, or the whole of, only placental tissue, e.g., components of a whole placenta, or components only of parts of a placenta, such as amniotic membrane, chorion, or combination of amniotic membrane and chorion, and the like. Similarly, the suspension can comprise components of a part of, or the whole of, only umbilical cord tissue, e.g., components of a whole umbilical cord, or components only of umbilical cord membrane, Wharton's jelly, umbilical vessels, or a combination thereof. In one embodiment, the suspension comprises components from an amniotic membrane. In another embodiment, the suspension comprises components from an umbilical cord membrane in combination with Wharton's jelly. The invention comprises suspension that are combinations of the foregoing, as well.

In other embodiments, the invention provides a suspension that comprises components of both placental tissue and umbilical cord tissue that are soluble in acidic or basic aqueous solution, and components that are insoluble in acidic or basic aqueous solution. For example, the suspension can comprise components of a whole placenta and a whole umbilical cord; components of a whole placenta and a portion of an umbilical cord (e.g., membrane only, membrane and Wharton's jelly only, Wharton's jelly only, umbilical vessels only, etc.); components of a whole umbilical cord and a portion of a placenta (e.g., components of amniotic membrane only, chorion only, amnion and chorion, etc.). In another embodiment, the suspension can also comprise components of a portion of a placenta and a portion of an umbilical cord, e.g., components of an amniotic membrane and components of an umbilical cord membrane; components of an amniotic membrane and components of an umbilical cord membrane and Wharton's jelly, components of an amniotic membrane and components of Wharton's jelly, and the like, in any combination.

In embodiments in which the suspension comprises components of both placental tissue and umbilical cord tissue, the components, either or both of components soluble or insoluble in acidic or basic aqueous solution, can be present in the suspension in any ratio. Thus, the suspension can comprise predominantly (i.e., greater than 50%) placental tissue components relative to umbilical cord tissue, or predominantly umbilical cord tissue components relative to placental tissue. In other embodiments, the suspension comprises about 1%, 2%, 3%, 4%, 5%, 10%, 20%, 30%, 40%, 50%, 60%, 70%, 80%, 90%, 95%, 96%, 97%, 98%, or about 99% placental components and/or umbilical cord components out of total placental and/or umbilical cord components in the suspension.

In another embodiment, the composition provided by the present invention is a solution comprising components of placental tissue and/or umbilical cord tissue that are soluble in basic or acidic aqueous solution. Generally, the solution lacks components of placental tissue and/or umbilical cord tissue that are insoluble in basic or acidic aqueous solution and removable by, e.g., centrifugation and/or filtration. For example, such solutions, according to the invention, comprise 0.5%, 0.1%, 0.05% or 0.01% or less placental tissue components and/or umbilical cord tissue components, insoluble in acidic or basic aqueous solution, by weight. Thus, in one embodiment, the invention provides a solution that comprises part or all of the fraction of placental tissue and/or umbilical cord tissue components that are soluble in aqueous solution and lacks components of placental tissue and/or umbilical cord tissue that are insoluble in acidic or basic aqueous solution.

In one embodiment, the invention provides a composition comprising placental and/or umbilical cord tissue components that are soluble neutral and acidic or neutral basic aqueous solution, and components that are insoluble in aqueous neutral and acidic or neutral and basic solution, wherein said composition is made by a process comprising the steps of (1) disrupting placental and/or umbilical cord tissue components in aqueous solution at neutral pH to form a suspension; (2) acidifying or basifying the suspension, (3) bringing said composition to neutral pH; and (4) removing tissue components insoluble in said aqueous solution at acidic and neutral pH, or at basic and neutral pH.

In certain embodiments, the solution comprises components of a part of, or the whole of, placental tissue, wherein the components are soluble in acidic or basic aqueous solution, e.g., components of a whole placenta, or components only of parts of a placenta, such as amniotic membrane, chorion, or combination of amniotic membrane and chorion, and the like. Similarly, the solution can comprise components of a part of, or the whole of, umbilical cord tissue, that are soluble in acidic or basic aqueous solution, e.g., components of a whole umbilical cord, or components only of umbilical cord membrane, Wharton's jelly, umbilical vessels, or a combination thereof. In one embodiment, the solution comprises components from an amniotic membrane that are soluble in acidic or basic aqueous solution. In another embodiment, the solution comprises components from an umbilical cord membrane in combination with Wharton's jelly that are soluble in aqueous solution. The invention comprises solutions that are combinations of the foregoing, as well.

In certain other embodiments, the invention provides a solution that comprises components of placental tissue and umbilical cord tissue that are soluble in acidic or basic aqueous solution. For example, the solution can comprise components, soluble in acidic or basic aqueous solution, of a whole placenta and a whole umbilical cord; components of a whole placenta and a portion of an umbilical cord (e.g., membrane only, membrane and Wharton's jelly only, Wharton's jelly only, umbilical vessels only, etc.); components of a whole umbilical cord and a portion of a placenta (e.g., components of amniotic membrane only, chorion only, amnion and chorion, etc.). In another embodiment, the solution can also comprise components, soluble in acidic or basic aqueous solution, of a portion of a placenta and a portion of an umbilical cord, e.g., components of an amniotic membrane and components of an umbilical cord membrane; components of an amniotic membrane and components of an umbilical cord membrane and Wharton's jelly, components of an amniotic membrane and components of Wharton's jelly, and the like, in any combination.

In embodiments in which the solution comprises components of both placental tissue and umbilical cord tissue, the components can be present in the solution in any ratio. Thus, the solution can comprise predominantly (i.e., greater than 50%) placental tissue components soluble in acidic and neutral, or basic and neutral, aqueous solution relative to umbilical cord tissue soluble in said solution, or predominantly umbilical cord tissue components soluble in acidic and neutral, or basic and neutral, aqueous solution relative to placental tissue soluble in said aqueous solution. In other embodiments, the solution comprises about 1%, 2%, 3%, 4%, 5%, 10%, 20%, 30%, 40%, 50%, 60%, 70%, 80%, 90%, 95%, 96%, 97%, 98%, or about 99% placental components and/or umbilical cord components, soluble in acidic and neutral, or basic and neutral, aqueous solution, out of a total of placental components and umbilical cord components soluble in said aqueous solution.

In various embodiments, the solutions comprise no more than about 0.1%, 0.2%, 0.3%, 0.4%, 0.5%, 0.6%, 0.7%, 0.8%, 0.9%, 1.0%, 1.2%, 1.4%, 1.6%, 1.8%, 2%, 3%, 4%, 5%, 6%, 7%, 8%, 9% or 10% placental tissue components, umbilical cord components, or a combination thereof, by weight. In other embodiments, the solutions comprise at least, about, or at most $1\times10^{-9}$, $5\times10^{-9}$, $1\times10^{-8}$, $5\times10^{-8}$, $1\times10^{-7}$, $5\times10^{-7}$, $1\times10^{-6}$, $5\times10^{-6}$, $1\times10^{-5}$, $5\times10^{-5}$, $10^{-4}$, $5\times10^{-4}$, $1\times10^{-3}$, $5\times10^{-3}$, $1\times10^{-2}$, $5\times10^{-2}$, or $1\times10^{-1}$ grams of tissue components, or a particular tissue component, or particular type of tissue component, per gram of composition or per milliliter of composition. Such tissue components can be, e.g., soluble proteins such as, e.g., cytokines or growth factors.

In another embodiment, the invention provides compositions comprising components of placental tissue and/or of umbilical cord tissue, soluble in acidic or basic aqueous solution, wherein the composition is a slurry, paste or gel. Generally, the components of placental tissue and/or of umbilical cord tissue, soluble in acidic or basic aqueous solution in the slurry or paste are the components, soluble in acidic or basic aqueous solution, of the solutions and suspensions described above. In various embodiments, such compositions are about 99%, 98%, 97%, 96%, 96%, 90%, 85%, 80%, 75%, 70%, 65%, 60%, 55%, 50%, 45%, 40%, 35%, 30%, 25%, 20%, 15%, 10%, 9%, 8%, 7%, 6%, 5%, 4%, 3%, 2% or about 1%, or are at least about, or at most about, 99.5%, 99%, 98%, 97%, 96%, 96%, 90%, 85%, 80%, 75%, 70%, 65%, 60%, 55%, 50%, 45%, 40%, 35%, 30%, 25%, 20%, 15%, 10%, 9%, 8%, 7%, 6%, 5%, 4%, 3%, 2% or about 1% water by weight. Similarly, in other embodiments, such compositions are about 99.5%, 99%, 98%, 97%, 96%, 96%, 90%, 85%, 80%, 75%, 70%, 65%, 60%, 55%, 50%, 45%, 40%, 35%, 30%, 25%, 20%, 15%, 10%, 9%, 8%, 7%, 6%, 5%, 4%, 3%, 2% or about 1%, or is at least about, or at most about, 99.5%, 99%, 98%, 97%, 96%, 96%, 90%, 85%, 80%, 75%, 70%, 65%, 60%, 55%, 50%, 45%, 40%, 35%, 30%, 25%, 20%, 15%, 10%, 9%, 8%, 7%, 6%, 5%, 4%, 3%, 2% or about 1% tissue components, insoluble at acidic and neutral pH, or insoluble at basic and neutral pH, by weight.

The invention further provides combinations of the above compositions. For example, a slurry, gel or paste can be combined with a homogenate; a solution can be combined with a homogenate; a solution can be combined with a slurry, paste, gel, etc. In such embodiments, the respective compositions can each be from the same individual, or can be from different individuals. For example, in a combination of a solution of the invention and a paste of the invention, the solution can be from placental tissue and/or umbilical cord tissue of a single individual or from a plurality of individuals, and the paste can be placental tissue and/or umbilical cord tissue of a single individual or from a plurality of individuals. In a preferred embodiment, the compositions are from a single individual. Other combinations of suspensions, solutions, slurries and/or pastes can be from single individuals or pluralities of individuals in like fashion.

5.1.2.3. Other Compositions of the Invention

The invention further provides compositions comprising placental tissue and/or umbilical cord tissue components soluble at neutral pH, e.g., obtained by disruption of tissue at neutral pH, in combination with placental tissue and/or umbilical cord components soluble at acidic and neutral pH or basic and neutral pH, e.g., obtained by acidification or basification and subsequent neutralization of tissue. These compositions comprise a suspension, solution, slurry, gel or paste, comprising such components soluble in aqueous solution at neutral pH in combination with a suspension, solution, slurry, gel or paste comprising such components soluble in acidic or basic solution. For example, a suspension of the invention comprising such components soluble at neutral pH can be combined, in any ratio, with a suspension of the invention comprising such components soluble at acidic or basic pH. Similarly, a solution of the invention comprising such components soluble at neutral pH can be combined, in any ratio, with a solution of the invention comprising such components soluble at acidic or basic pH.

5.1.3. Methods of Making Compositions of the Invention

The invention further provides methods of making the compositions of the present invention.

5.1.3.1. Suspensions and Solutions

In one embodiment, the invention provides a method of making a suspension from placental tissue, umbilical cord tissue, or a combination thereof, comprising disrupting, e.g., homogenizing, such tissue in aqueous solution at neutral pH. Disruption of placental tissue, umbilical cord tissue, or combination thereof, can be accomplished by any art-recognized method of disrupting tissue, such as maceration, homogenization, use of a blender, sonication, and the like. Preferably, during disruption, the temperature of the suspension is kept below room temperature, e.g., below 25° C., more preferably below about 10° C., and more preferably between about 10° C. and the freezing point of the solution in which the placental tissue or umbilical cord tissue is disrupted.

The aqueous solution in which the tissue is disrupted can comprise one or more compositions that act to reduce protein degradation. For example, the solution can comprise one or more protease inhibitors. The solution can also comprise one or more antioxidants, e.g., thiourea, sodium bisulfite, sodium metabisulfite, and the like. The solution can comprise one or more chelators, e.g., EDTA and/or EGTA.

The time for which the placenta, umbilical cord, placental tissue, umbilical cord tissue, or combination thereof, is contacted with a pH-neutral aqueous solution affects the concentration of the components soluble in aqueous solution, with a longer contact time generally leading to a more concentrated solution. Such contact can take place for, e.g., about 1, 2, 3, 4, 5, 6, 7, 8, 9, 10, 15, 20, 25, 30, 35, 40, 45, 50 or 55 minutes, or about 1, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, 20, 21, 22, or 23 hours, or about 1, 2, 3, 4, 5, 6 days. The degree of disruption can also affect the concentration of such components.

In another embodiment, the invention provides a method of preparing a solution comprising placental or umbilical membrane components soluble at neutral pH, comprising contacting placental tissue, umbilical cord tissue, or combination thereof, with a pH-neutral aqueous solution; disrupting the placental tissue, umbilical cord tissue, or combination thereof in said solution to form a suspension, and removing substantially all of the solid material in said suspension to form a solution. Generally, the solution is made after making the suspension, as described above. As used herein, "substantially all solid material" means at least 99%, preferably at least 99.5%, more preferably 99.9% of the weight of the starting placental or umbilical cord material used to make the suspension. In one embodiment, the method comprises disrupting umbilical cord membrane comprising Wharton's jelly in the solution. In other embodiments, a combination of umbilical cord membrane and placental tissue, e.g., amniotic membrane, is used to make the solution. In other embodiments the solution is made with placental tissue only. In embodiments in which both umbilical cord tissue and placental tissue are used, the umbilical cord tissue and placental tissue are from the same individual. In other embodiments in which both umbilical cord tissue and placental tissue are used, the placental tissue and umbilical tissue are from different individuals.

The solution used for disruption of placental tissue, umbilical cord tissue, or combination thereof, can be any pharmaceutically-acceptable solution pH-neutral, e.g., a solution suitable for ocular, topical or internal use. Such solutions include, e.g., sterile, deionized water, a buffer solution (e.g., phosphate-buffered saline, carbonate buffer, or the like), a saline solution (e.g., a 0.9% saline solution), or the like.

In the method of making a solution of the invention, various aspects can be altered to change the concentration of the components, soluble in aqueous solution, present in the final solution. For example, the ratio of the weight of placenta and/or umbilical cord material to volume of solution, in which the tissue is disrupted, can be varied; a low ratio will produce a solution with a relatively low concentration of components that are soluble in aqueous solution, and a high ratio will produce a solution with a relatively high concentration of components, soluble in aqueous solution, in the final solution. In one embodiment, for example, the ratio of aqueous solution to wet solid (that is, wet placental tissue and/or umbilical cord tissue) is between about 1:100 and about 1000:1, preferably between about 1:20 and about 600:1. In various embodiments, for example, the ratio of solution to wet solid weight (w/w) is about 1:100, 1:90, 1:80, 1:70, 1:60, 1:50, 1:40, 1:30, 1:20, 1:15, 1:10, 1:5, 1:1, 5:1, 10:1, 15:1, 20:1, 25:1, 30:1, 35:1, 40:1, 45:1, 50:1, 60:1, 70:1, 80:1, 90:1, 100:1, 125:1, 150:1, 175:1, 200:1, 250:1, 300:1, 350:1, 400:1, 450:1, 500:1, 550:1, 600:1, 700:1, 800:1, 900:1 or about 1000:1. In another embodiment, for example, a placental tissue or umbilical cord tissue is disrupted in about 1, 2, 3, 4, 5, 6, 7, 8, 9, or 10 liters of solution. In specific embodiments, the placental tissue is amniotic membrane, chorion, or amnion and chorion. In another specific embodiment, the amniotic membrane, chorion, or amnion and chorion are from a single placenta. In another specific embodiment, the amniotic membrane, chorion, or amnion and chorion are from a plurality of placentas. In another specific embodiment, the umbilical cord tissue is umbilical cord membrane, Wharton's jelly, or umbilical vessels, or a combination thereof. As for the placental tissue, the umbilical cord tissue can be derived from a single umbilical cord or a plurality of umbilical cords. In particular embodiments, the ratio of weight of placental tissue, umbilical cord tissue or combination thereof to the volume of solution is about 1:1 to about 1:10.

Removal of the solid components of the suspension can be accomplished by any means known to those of skill in the art, including, e.g., centrifugation or filtration. Centrifugation can be accomplished using any commercially-available centrifugation apparatus; preferably, the centrifuge accepts bottles or other containers able to contain 100 ml or more of solution to facilitate batch processing or clarification of larger volumes of suspension. Similarly, filtration can be accomplished using any art-recognized method, such as forced filtration or vacuum filtration. Preferably a filtration apparatus used to accomplish such filtration has the capacity to process at least 1, 2, 3, 4, 5, 6, 7, 8, 9, 10 liters or more of solution per hour, and comprises a filter that does not adsorb biomolecules. In embodiments, filtration or centrifugation removes suspended matter in the suspension wherein the suspended matter is larger than about 500 microns, 250 microns, 200 microns, 100 microns, 75 microns, 50 microns or 25 microns.

The invention further encompasses a pH shifting method of preparing a suspension of the invention comprising contacting placental tissue and/or umbilical cord tissue with an acidic or basic aqueous solution to solubilize tissue components that are soluble in acidic or basic aqueous solution. The method generally comprises, in either order, disruption, e.g., homogenization of placental and/or umbilical cord tissue and contacting the tissue with an acidic or basic solution; allowing the solution to disrupt the tissue; and shifting the pH of the solution to neutral pH.

In one embodiment of the pH shifting method, placental tissue, umbilical cord tissue, or combination thereof, is contacted with an acidic or basic solution and disrupted, e.g., homogenized, as described above, to produce a suspension. The tissue can either be contacted with the acidic or basic solution and disrupted, or disrupted at neutral pH and then contacted with an acidic or basic solution, e.g., the solution in which the tissue is disrupted can be acidified or basified. Preferably, the solution with which the placental tissue or umbilical tissue is contacted is buffered so that acidic or basic pH is easily maintained. The resulting suspension is then, after a period of time, brought to neutral pH (that is, about pH 7.0 to about pH 7.4).

The acid used in this method can be any acid, and can be, e.g., hydrochloric acid, phosphoric acid, acetic acid, sulfuric acid, picric acid, iodic acid, periodic acid, hydroiodic acid, bromic acid, hydrobromic acid, perbromic acid, hydrofluoric acid, chloric acid, perchloric acid, nitric acid, and the like. Acetic acid and HCl are preferred. Extremely strong acids, such as fluoroantimonic acid, magic acid or fluorosulfuric acid can also be used, but are not preferred. Weak acids can also be used, such as nicotinic acid, salicylic acid, pyruvic acid, or ethanoic acid. The base can be any base, e.g., sodium hydroxide, sodium acetate, ammonium hydroxide, potassium hydroxide, barium hydroxide, cesium hydroxide, strontium hydroxide, calcium hydroxide or lithium hydroxide. Extremely strong bases can also be used, e.g., sodium hydride, lithium diisopropylamide or lithium amide. Sodium hydroxide and sodium acetate are preferred bases.

In certain embodiments, an amount of acid or base is used to acidify the solution to between about pH 4 and about pH 6, or to basify the solution to between about pH 8 and about pH 10. In other embodiments, the solution is acidified to about pH 6.0, about pH 5.3, about pH 5.0, about pH 4.3, about pH 4.0, about pH 3.3 or about pH 3.0. In other embodiments, the solution is basified to about pH 8.0, about pH 8.3, about pH 9.0, about pH 9.3, about pH 10, about pH 10.3, or about pH 11.

The strength (e.g., normality or molarity) of the base or acid used is not critical; however, a dilute acid or base is preferable to a more concentrated base or acid so as to avoid local concentrations of acid or base, during acidification or basification, that are potentially damaging, e.g., to aqueous solution-soluble proteins. In various embodiments, an acid or base used to acidify or basify the solution is between about 0.1N and about 6N acid or base, or between about 0.1M and about 6M acid or base. In a specific embodiment, the acid is about 1N or about 1M.

The placental or umbilical cord tissue, or combination thereof, is contacted with the acidic or basic solution for a time sufficient for the solution to cause a disruption of the placental or umbilical cord tissue over and above that caused by physical disruption of the tissue. For example, such additional disruption can occur when the placental or umbilical cord tissue is contacted with the acidic or basic solution for at least about 1, 2, 3, 4, 5, 10, 15, 20, 25, 30, 35, 40, 45, 50 or 55 minutes, or for at least about 1, 2, 3, 4, 5, 6, 7, 8, 9, 10, 11, 12, 13, 14, 15, 16, 17, 18, 19, 20, 21, 22 or 23 hours, or for at least about 1, 2, 3 or more days. Preferably, the placental tissue and/or umbilical cord tissue is disrupted at a temperature of between about the freezing point of the solution and about 10° C.

Neutralization of the acidic or basic homogenate can be accomplished by any means known in the art. For example, an acidic solution can be brought to neutral pH by the addition of an appropriate amount of, e.g., NaOH. A basic solution can be neutralized by the addition of an appropriate amount of, e.g., hydrochloric acid. In certain embodiments, the base chosen to neutralize an acidic solution, or the acid chosen to neutralize a basic solution, results in the formation of a water-soluble salt. Preferred acid/base pairs include HCl and NaOH; HAc and NaOH; and HAc and NaAc.

The resulting suspension can be used without further modification. In an embodiment in which the suspension is to be used for a medical purpose, the suspension is treated to remove concentrations of salt above physiological, e.g., by dialysis or by passage over a desalting column.

The invention further provides a method of making a solution of the invention. In one embodiment, a suspension made as described above by the pH shifting method can be clarified, for example, by centrifugation and/or filtration to substantially remove the solid components of the suspension, thereby producing a solution of the invention. In certain embodiments, filtration or centrifugation removes particulate matter in the suspension wherein the particulate matter is larger on average than about 500 microns, 250 microns, 200 microns, 100 microns, 75 microns, 50 microns or 25 microns in diameter. The resulting solution comprises components (that is, proteins, lipids, glycolipids, glycoproteins, and the like) of placental tissue, umbilical cord tissue or a combination thereof, wherein the components are soluble in an acidic solution or a basic solution, and substantially lacks placental tissue or umbilical tissue components insoluble in an acidic or basic solution.

Thus, in one embodiment, the invention provides a method of preparing a composition, comprising: (a) in either order: (i) contacting placental tissue, umbilical cord tissue or a combination thereof, with an acidic or basic solution; (ii) disrupting the placental tissue, umbilical cord tissue or a combination thereof in said solution to form a suspension; (b) bringing the suspension to neutral pH; and (c) removing particulate matter within said suspension. In another embodiment, the invention provides a method of preparing a composition, comprising (a) contacting placental tissue, umbilical cord tissue, or a combination thereof, with an acidic or basic solution; (b) disrupting the tissue in said solution to form a suspension; and (c) bringing the suspension to a neutral pH. In a specific embodiment of the latter method, the method additionally comprises removing particulate matter within said suspension after step (c). In a specific embodiment of either method, the acidic solution is an acetic acid solution. In another specific embodiment, the acidic solution is between about pH 3.0 and about pH 6.0. In another specific embodiment, the acidic solution is between about pH 4.5 and about pH 6.0. In another specific embodiment, said basic solution is a sodium hydroxide solution. In another specific embodiment, said basic solution is between about pH 8.0 and pH 11.0. In another specific embodiment, said basic solution is between about pH 80. and pH 9.5. In another specific embodiment, said disrupting is performed at a temperature of between about 10° C. and the freezing point of the solution in which said tissue is disrupted.

5.1.3.2. Slurries, Pastes and Gels

The invention further provides methods of making slurries, gels and pastes from the placental tissue components and/or umbilical tissue components described above.

The water content of any of the compositions described in Section 4.1.2, above, in certain embodiments, is adjusted, e.g., the water content increased or reduced. In embodiments in which the water content is reduced, water can be removed from the composition by any method known to the art. For example, water can be removed by evaporation or lyophilization. Water can be removed from the solution such that the water content of the composition is about 99.5%, 99%, 98%, 97%, 96%, 96%, 90%, 85%, 80%, 75%, 70%, 65%, 60%, 55%, 50%, 45%, 40%, 35%, 30%, 25%, 20%, 15%, 10%, 9%, 8%, 7%, 6%, 5%, 4%, 3%, 2% or about 1%, or is at least about, or at most about, 99.5%, 99%, 98%, 97%, 96%, 96%, 90%, 85%, 80%, 75%, 70%, 65%, 60%, 55%, 50%, 45%, 40%, 35%, 30%, 25%, 20%, 15%, 10%, 9%, 8%, 7%, 6%, 5%, 4%, 3%, 2% or about 1% water by weight. Similarly, water can be removed from the composition such that the solid content of the composition is about 99.5%, 99%, 98%, 97%, 96%, 96%, 90%, 85%, 80%, 75%, 70%, 65%, 60%, 55%, 50%, 45%, 40%, 35%, 30%, 25%, 20%, 15%, 10%, 9%, 8%, 7%, 6%, 5%, 4%, 3%, 2% or about 1%, or is at least about, or at most about, 99.5%, 99%, 98%, 97%, 96%, 96%, 90%, 85%, 80%, 75%, 70%, 65%, 60%, 55%, 50%, 45%, 40%, 35%, 30%, 25%, 20%, 15%, 10%, 9%, 8%, 7%, 6%, 5%, 4%, 3%, 2% or about 1% solid by weight.

The invention, in one embodiment, provides pastes comprising placental components, umbilical cord components, or a combination thereof, that are soluble in aqueous solution (either at neutral pH, or at acidic and neutral pH or basic and neutral pH). In a specific embodiment, water is removed from a solution made from the solution made from placental tissue, umbilical tissue or a combination thereof, described above, until the remaining placental or umbilical cord material becomes paste-like. As water is removed from the composition, solutes, such as proteins, start to precipitate to form a slurry. As the water content of the composition is reduced below about 10%, the composition becomes paste-like. In one embodiment, water is removed until the water content of the composition is between about 1% and about 20%, preferably between about 3% and about 10%. In another specific embodiment, the solution comprising placental tissue components, umbilical cord components or a combination thereof can be substantially dehydrated, that is, dehydrated until further water cannot be removed or until the remaining material in solution appears dry, e.g., until the water content of the material is about 1% or less.

Dehydration of the solution can be accomplished by any method known in the art, such as vacuum drying or lyophilization. Preferably, vacuum drying is carried out at a temperature of between about 10° C. and the freeing point of the solution, e.g., about 4° C. Vacuum drying is preferred for larger volumes of solution, e.g., volumes of 100 ml and larger. Lyophilization can be accomplished by any art-accepted method; see, e.g., U.S. Pat. No. 4,001,944. For example, the clarified solution can be quickly frozen in 100% ethanol and dry ice, then lyophilized at −20° C. in a sterile lyophilizer until dry.

Once substantially dehydrated, the material can, for example, be reconstituted into a paste or solution by adding the appropriate amount of liquid, e.g., water, buffer, saline solution, and the like. In one embodiment, the dried water-soluble placental material or umbilical cord material can be supplemented with another composition, preferably a composition present in, or derived from, a collagen-containing tissue. For example, the dried placental material or umbilical cord material, soluble in aqueous solution, can be supplemented with, e.g., a collagen composition such as purified collagen, dried and pulverized collagen-containing tissue, e.g., pericardium, dura mater, skin, amniotic membrane, umbilical cord membrane, intestine, and the like. In one embodiment, placental and/or umbilical cord tissue components supplemented by an amount of purified collagen not to exceed, e.g., 100 times the weight of the amniotic membrane material obtained from the amniotic membrane solution, and water is added so as to achieve between 3% and 10% water by weight. The water, tissue material and purified collagen are thoroughly mixed to form a paste.

In another embodiment, the placental material or umbilical cord material that is soluble in aqueous solution is supplemented with placental or umbilical cord material, insoluble in soluble in aqueous solution (neutral, acidic or basic) removed, e.g., by centrifugation and/or filtration during production of the solution, as described above. In certain embodiments, supplementation using such material results in the formation of a composition having relatively less or more insoluble material than is present in the placental or umbilical cord suspension from which the material, soluble in pH neutral, or acidic or basic, aqueous solution, was originally obtained.

In various embodiments, the ratio of the weight of the soluble placental tissue or umbilical tissue components to the supplemental materials is, e.g., about 1:1, 1:2, 1:3, 1:4, 1:5, 1:6, 1:7, 1:8, 1:9, 1:10, 1:15, 1:20, 1:30, 1:40, 1:50, 1:60, 1:70, 1:80, 1:90 or about 1:100. The dried soluble placental material or umbilical cord material can also be supplemented with other biomolecules, e.g., fibronectin, laminin, or other extracellular matrix proteins; other proteins such as cytokines, growth factors, and the like; lipids, glycoproteins, glycolipids, hyaluronic acid, glycosaminoglycans, and the like.

The dried water-soluble placental material or umbilical cord material, alone or supplemented as described above, can, for example, be combined with a liquid, e.g., water, buffer, saline solution, or the like, to achieve a water content of between about 3% and about 10% to form a paste.

In another embodiment, the invention provides gels comprising, e.g., any of the suspensions, solutions, or soluble components of placental tissue or umbilical cord tissue of the invention. In one embodiment, the gel comprises placental material and/or umbilical cord material that is soluble in aqueous solution, supplemented with placental or umbilical cord material, insoluble in soluble in aqueous solution (neutral, acidic or basic) removed, e.g., by centrifugation and/or filtration during production of the solution, as described above. In certain embodiments, supplementation using such material results in the formation of a composition having relatively less or more insoluble material than is present in the placental or umbilical cord suspension from which the material, soluble in pH neutral, or acidic or basic, aqueous solution, was originally obtained.

In one embodiment, a gelling compound is added in a weight/weight ratio to a composition of the invention at a weight/weight or weight/volume ratio of about 1:10 to about 10:1. In another embodiment, a gelling compound is added in an amount such that the water content of the resulting gel to about 60% to about 99% by weight In embodiments in which the composition is dehydrated, water is then added to the composition and gelling compound in an amount that brings the water content of the resulting gel to about 60% to about 99% by weight. In various embodiments, the ratio in the gel of the weight of the soluble placental tissue or umbilical tissue components to the supplemental materials is, e.g., about 1:1, 1:2, 1:3, 1:4, 1:5, 1:6, 1:7, 1:8, 1:9, 1:10, 1:15, 1:20, 1:30, 1:40, 1:50, 1:60, 1:70, 1:80, 1:90 or about 1:100. The dried soluble placental material or umbilical cord material can also be supplemented with other biomolecules, e.g., fibronectin, laminin, or other extracellular matrix proteins; other proteins such as cytokines, growth factors, and the like; lipids, glycoproteins, glycolipids, hyaluronic acid, glycosaminoglycans, and the like.

Gelling agents, and methods of making gels from solutions, are well-known in the art. Examples of gelling agents that can be used to make the gels of the invention include, but are not limited to, hydroxymethylcellulose, hydroxyethylcellulose, methylcellulose, hydroxypropylmethylcellulose, polyvinyl alcohol, polyvinylpyrrolidone, pectin, agar, alginic acid, alginate, amylose, high amylose starch, gum arabic, carrageenan, processed euchema seaweed, casein, carboxymethyl cellulose, carboxyvinyl copolymer, hydroxypropylcellulose, microcrystalline cellulose, sodium carboxymethyl cellulose, natural celluloses, chitin, chitosan, collagen, dextran, polydextran, elsinan, gelatin, gellan gum, guar gum, gelatin, ghatti gum, karaya gum, gluten, konjac, levan, locust bean gum, maltodextrin, methylmethacrulate copolymer, oat gum, pectin, low methoxy pectin, polyethylene glycol, polylysine, polybrene, polyacrylic acid, propylene glycol, protein, pullulan, starch, modified starches, soy protein, tara gum, tamarind gum, tragacanth, whey protein, xanthan gum, zein, and the like. Typically, the gelling agents are employed in amount of about 0.3 to about 30 weight percent.

In certain embodiments, the gel of the invention comprises a crosslinking agent. In a specific embodiment, the crosslinking agent is riboflavin. In another specific embodiment, the matrix of the gel comprising the riboflavin comprises collagen. The riboflavin can be used, e.g., to crosslink collagen proteins in a collagen-containing gel, e.g., to improve or increase the mechanical strength of the gel. Such gels would be useful in, e.g., wound healing, wherein the wound to be healed experiences mechanical forces such as, e.g., stretching, rotation, and the like.

In certain embodiments, the invention provides a method of making a gel, comprising contacting a gel of the invention with riboflavin, wherein said gel comprises a matrix comprising collagen, and exposing the gel to ultraviolet light (UVA) for a time and in an amount sufficient for a plurality of the collagen molecules in the gel to become crosslinked. The gel comprising the collagen matrix to be crosslinked can be produced so as to include riboflavin during manufacture. The riboflavin can also be added to the gel at any time prior to crosslinking, e.g., immediately before crosslinking, e.g., by immersion of the gel in a solution of riboflavin. Such a riboflavin solution can be about 0.01% to about 1% riboflavin, e.g., about 0.1% riboflavin (weight/volume). As riboflavin is sensitive to light, the gel comprising riboflavin is preferably handled or processed in the dark prior to crosslinking. In certain embodiments, the gel comprising riboflavin are crosslinked by exposure to UVA light for about 10 to about 60 minutes, about 20 to about 40 minutes, or for about 30 minutes. In certain other embodiments, the maximum irradiance for crosslinking is about 2.0 mW/cm$^2$, about 2.5 mW/cm$^2$, or about 3.0 mw/cm$^2$.

Other compositions of the invention, to the extent they comprise collagens, can be treated with riboflavin in the same manner to crosslink the collagen proteins.

5.1.4. Formulations

The compositions described above can be formulated for use in any medical context.

Solutions made from placental tissue or umbilical cord tissue as described herein can, for example, be formulated as eye drops. In one embodiment, the solution used to make eye drops is a solution obtained from disruption, e.g., homogenization, of placental tissue and/or umbilical cord tissue, wherein the solution comprises placental tissue components, umbilical cord components, or both, that are soluble in aqueous solution (either at neutral pH, or at basic and neutral pH or acidic and neutral pH), and substantially lacks placental tissue components and/or umbilical cord components that are insoluble in said aqueous solution. In a specific embodiment, the components substantially lack acid- or base-insoluble placental tissue components or umbilical cord tissue components. In yet another embodiment, the placental tissue is amniotic membrane. In another more specific example, the umbilical cord tissue is umbilical cord membrane and Wharton's jelly.

The solutions described herein, used as eye drops, can comprise other compounds suitable for ocular use. For example, in one embodiment, the solution can comprises an ophthalmologically-acceptable liquid or solution. In another embodiment, the solution comprises saline solution, glycerin, hypromellose, or polyethylene glycol, or a combination of any of the foregoing. In a more specific embodiment, the solution comprises saline solution, glycerin, hypromellose, and polyethylene glycol. In another specific example, the solution comprises a lubricant. In a more specific example, the lubricant is hydrophobic. In another specific example, the lubricant is hydrophilic. In another specific example, the solution comprises an antibiotic, an analgesic, and anti-inflammatory compound.

In other embodiments, the compositions of the invention, e.g., the solutions provided herein, or the soluble placental tissue components, umbilical tissue components or combination thereof in the solutions, can be formulated into creams, ointments or other medically-useful forms, including transdermal, topical, and mucosal forms including, but not limited to, sprays, aerosols, creams, lotions, ointments, emulsions, or other forms. Such forms, and methods of preparing such forms, are known to those of skill in the art. See, e.g., *Remington: The Science and Practice of Pharmacy*, 20th ed., Lippincott Williams & Wilkins, Baltimore, Md. (2000); and *Introduction to Pharmaceutical Dosage Forms*, 4th ed., Lea & Febiger, Philadelphia (1985). Forms suitable for contacting mucosal tissues within the oral cavity can be formulated as mouthwashes or as oral gels.

Suitable excipients (e.g., carriers and diluents) and other materials that can be used to provide transdermal, topical, and mucosal forms encompassed by this invention are well known to those skilled in the pharmaceutical arts, and depend on the particular tissue to which a given form will be applied. Typical excipients include, but are not limited to, water, acetone, ethanol, ethylene glycol, propylene glycol, butane-1,3-diol, isopropyl myristate, isopropyl palmitate, mineral oil, and mixtures thereof to form lotions, tinctures, creams, emulsions, gels or ointments, which are non-toxic and pharmaceutically acceptable. Moisturizers or humectants can also be added to pharmaceutical compositions and dosage forms if desired. Examples of such additional ingredients are well known in the art. See, e.g., *Remington: The Science and Practice of Pharmacy*, 20th ed., Lippincott Williams & Wilkins, Baltimore, Md. (2000).

Sterilization of the compositions of the invention can be accomplished by any means known in the art for sterilizing similar compositions; however, sterilization methods that generally do not deactivate proteins or polypeptides are preferred. For example, the solutions of the invention can be sterilized by, e.g., filtration. Such a filter preferably excludes at least bacteria, and preferably excludes bacteria and viruses, e.g., a filter having a pore size of less than about 0.45 microns or a filter having a pore size of less than about 20 nanometers. To the extent that the gels, slurries and/or pastes of the present invention are made from the solutions of the invention and additional components, the solutions can be filtered, and the additional components can be sterilized, e.g., by filtration, heat, radiation, sterilizing chemical, etc., as appropriate for the component.

Sterility of the compositions of the invention is greatly enhanced by topical sterilization of placental and/or umbilical cord tissues used to prepare the compositions of the invention. For example, placental and/or umbilical cord tissues can be thoroughly swabbed with a disinfectant such as 70% alcohol during collection and processing steps prior to making the compositions of the invention.

5.1.5. Bioactive Compounds

The compositions of the invention can comprise one or more bioactive or medicinal compounds, such as small organic molecules (e.g., drugs), antibiotics, antiviral agents, antimicrobial agents, anti-inflammatory agents, antiproliferative agents, cytokines, enzyme or protein inhibitors, antihistamines, and the like. In various embodiments, the compositions may comprise antibiotics (such as Clindamycin, Minocycline, Doxycycline, Gentamycin), hormones, growth factors, anti-tumor agents, anti-fungal agents, anti-viral agents, pain medications (including XYLOCAINE®, Lidocaine, Procaine, Novocaine, etc.), antihistamines (e.g., antazoline, azelastine, diphenhydramine, BENADRYL®, emedastine, levocabastine, phenylephrine HCL, naphazoline HCL, toxymetazoline HCL, tetrahydrozoline HCL, etc.), anti-inflammatory agents, anti-infectives including but not limited to silver (such as silver salts, including but not limited to silver nitrate and silver sulfadiazine), elemental silver, antibiotics, bactericidal enzymes (such as lysozome), wound healing agents (such as cytokines including but not limited to PDGF (e.g., REGRANEX®), TGF; thymosin), hyaluronic acid as a wound healing agent, wound sealants (such as fibrin with or without thrombin), cellular attractant and scaffolding reagents (such as fibronectin), and the like, or combinations of any of the foregoing, or of the foregoing and other compounds not listed. A person of skill in the art will know which compounds are useful for specific applications, e.g., which compounds are useful for ocular applications of the compositions of the invention.

The compositions of the invention can comprise any of the compounds listed herein, without limitation, individually or in any combination. Any of the bioactive compounds listed herein may be formulated by known methods for immediate release or extended release. Additionally, the placental biomaterial may comprise two or more biologically active compounds in different manners; e.g., the biomaterial or membrane may be impregnated with one biologically active compound and coated with another. In another embodiment, the placental biomaterial comprises one biologically active compound formulated for extended release, and a second biologically active compound formulated for immediate release.

Wound healing requires adequate nutrition, particularly the presence of iron, zinc, vitamin C, arginine, and the like. Thus, the compositions of the invention can comprise a physiologically-available form of one or more nutrients required for wound healing. Preferably, the nutrient is formulated for extended release.

The compositions of the invention can comprise an antibiotic. In certain embodiments, the antibiotic is a macrolide (e.g., tobramycin (TOBI®)), a cephalosporin (e.g., cephalexin (KEFLEX®)), cephradine (VELOSEF®)), cefuroxime (CEFTIN®, cefprozil (CEFZIL®), cefaclor (CECLOR®), cefixime (SUPRAX® or cefadroxil (DURICEF®), a clarithromycin (e.g., clarithromycin (Biaxin)), an erythromycin (e.g., erythromycin (EMYCIN®)), a penicillin (e.g., penicillin V (V-CILLINK® or PEN VEEK®)) or a quinolone (e.g., ofloxacin (FLOXIN®), ciprofloxacin (CIPRO®) omorfloxacin (NOROXIN®)), aminoglycoside antibiotics (e.g., apramycin, arbekacin, bambermycins, butirosin, dibekacin, neomycin, neomycin, undecylenate, netilmicin, paromomycin, ribostamycin, sisomicin, and spectinomycin), amphenicol antibiotics (e.g., azidamfenicol, chloramphenicol, florfenicol, and thiamphenicol), ansamycin antibiotics (e.g., rifamide and rifampin), carbacephems (e.g., loracarbef), carbapenems (e.g., biapenem and imipenem), cephalosporins (e.g., cefaclor, cefadroxil, cefamandole, cefatrizine, cefazedone, cefozopran, cefpimizole, cefpiramide, and cefpirome), cephamycins (e.g., cefbuperazone, cefinetazole, and cefminox), monobactams (e.g., aztreonam, carumonam, and tigemonam), oxacephems (e.g., flomoxef, and moxalactam), penicillins (e.g., amdinocillin, amdinocillin pivoxil, amoxicillin, bacampicillin, benzylpenicillinic acid, benzylpenicillin sodium, epicillin, fenbenicillin, floxacillin, penamccillin, penethamate hydriodide, penicillin o-benethamine, penicillin 0, penicillin V, penicillin V benzathine, penicillin V hydrabamine, penimepicycline, and phencihicillin potassium), lincosamides (e.g., clindamycin, and lincomycin), macrolides (e.g., azithromycin, carbomycin, clarithomycin, dirithromycin, erythromycin, and erythromycin acistrate), amphomycin, bacitracin, capreomycin, colistin, enduracidin, enviomycin, tetracyclines (e.g., apicycline, chlortetracycline, clomocycline, and demeclocycline), 2,4-diaminopyrimidines (e.g., brodimoprim), nitrofurans (e.g., furaltadone, and furazolium chloride), quinolones and analogs thereof (e.g., cinoxacin, ciprofloxacin, clinafloxacin, flumequine, and grepagloxacin), sulfonamides (e.g., acetyl sulfamethoxypyrazine, benzylsulfamide, noprylsulfamide, phthalylsulfacetamide, sulfachrysoidine, and sulfacytine), sulfones (e.g., diathymosulfone, glucosulfone sodium, and solasulfone), cycloserine, mupirocin and tuberin.

The compositions of the invention can comprise an antifungal agent. Suitable antifungal agents include but are not limited to amphotericin B, itraconazole, ketoconazole, fluconazole, intrathecal, flucytosine, miconazole, butoconazole, clotrimazole, nystatin, terconazole, tioconazole, ciclopirox, econazole, haloprogrin, naftifine, terbinafine, undecylenate, and griseofuldin.

The compositions of the invention can comprise an anti-inflammatory agent. Useful anti-inflammatory agents include, but are not limited to, non-steroidal anti-inflammatory drugs such as salicylic acid, acetylsalicylic acid, methyl salicylate, diflunisal, salsalate, olsalazine, sulfasalazine, acetaminophen, indomethacin, sulindac, etodolac, mefenamic acid, meclofenamate sodium, tolmetin, ketorolac, dichlofenac, ibuprofen, naproxen, naproxen sodium, fenoprofen, ketoprofen, flurbinprofen, oxaprozin, piroxicam, meloxicam, ampiroxicam, droxicam, pivoxicam, tenoxicam, nabumetome, phenylbutazone, oxyphenbutazone, antipyrine, aminopyrine, apazone and nimesulide; leukotriene antagonists including, but not limited to, zileuton, aurothioglucose, gold sodium thiomalate and auranofin; and other anti-inflammatory agents including, but not limited to, methotrexate, colchicine, allopurinol, probenecid, sulfinpyrazone and benzbromarone.

The compositions of the invention can comprise an antiviral agent. Useful antiviral agents include, but are not limited to, nucleoside analogs, such as zidovudine, acyclovir, gangcyclovir, vidarabine, idoxuridine, trifluridine, and ribavirin, as well as foscarnet, amantadine, rimantadine, saquinavir, indinavir, ritonavir, and the alpha-interferons.

The compositions of the invention can comprise a cytokine receptor modulator. Examples of cytokine receptor modulators include, but are not limited to, soluble cytokine receptors (e.g., the extracellular domain of a TNF-$\alpha$ receptor or a fragment thereof, the extracellular domain of an IL-10 receptor or a fragment thereof, and the extracellular domain of an IL-6 receptor or a fragment thereof), cytokines or fragments thereof (e.g., interleukin (IL)-2, IL-3, IL-4, IL-5, IL-6, IL-7, IL-8, IL-9, IL-10, IL-11, IL-12, IL-15, TNF-$\alpha$, TNF-$\beta$, interferon (IFN)-$\alpha$, IFN-$\beta$, IFN-$\gamma$, and GM-CSF), anti-cytokine receptor antibodies (e.g., anti-IFN receptor antibodies, anti-IL-2 receptor antibodies (e.g., Zenapax (Protein Design Labs)), anti-IL-4 receptor antibodies, anti-IL-6 receptor antibodies, anti-IL-10 receptor antibodies, and anti-IL-12 receptor antibodies), anti-cytokine antibodies (e. g., anti-IFN antibodies, anti-TNF-$\alpha$ antibodies, anti-IL-10 antibodies, anti-IL-6 antibodies, anti-IL-8 antibodies (e.g., ABX-IL-8 (Abgenix)), and anti-IL-12 antibodies). In a specific embodiment, a cytokine receptor modulator is IL-4, IL-10, or a fragment thereof. In another embodiment, a cytokine receptor modulator is an anti-IL-1 antibody, anti-IL-6 antibody, anti-IL-12 receptor antibody, or anti-TNF-$\alpha$ antibody. In another embodiment, a cytokine receptor modulator is the extracellular domain of a TNF-$\alpha$ receptor or a fragment thereof. In certain embodiments, a cytokine receptor modulator is not a TNF-$\alpha$ antagonist.

In one embodiment, proteins, polypeptides or peptides (including antibodies) that are utilized as immunomodulatory agents are derived from the same species as the recipient of the proteins, polypeptides or peptides so as to reduce the likelihood of an immune response to those proteins, polypeptides or peptides. In another embodiment, when the subject is a human, the proteins, polypeptides, or peptides that are utilized as immunomodulatory agents are human or humanized.

The compositions of the invention can comprise a cytokine. Examples of cytokines include, but are not limited to, colony stimulating factor 1 (CSF-1), interleukin-2 (IL-2), interleukin-3 (IL-3), interleukin-4 (IL-4), interleukin-5 (IL-5), interleukin-6 (IL-6), interleukin-7 (IL-7), interleukin-9 (IL-9), interleukin-10 (IL-10), interleukin-12 (IL-12), interleukin 15 (IL-15), interleukin 18 (IL-18), insulin-like growth factor 1 (IGF-1), platelet derived growth factor (PDGF), erythropoietin (Epo), epidermal growth factor (EGF), fibroblast growth factor (FGF) (basic or acidic), granulocyte macrophage stimulating factor (GM-CSF), granulocyte colony stimulating factor (G-CSF), heparin binding epidermal growth factor (HEGF), macrophage colony stimulating factor (M-CSF), prolactin, and interferon (IFN), e.g., IFN-alpha, and IFN-gamma), transforming growth factor alpha (TGF- α), TGFβ1, TGFβ2, tumor necrosis factor alpha (TNF-α), vascular endothelial growth factor (VEGF), hepatocyte growth factor (HGF), etc.

The compositions of the invention can comprise a hormone. Examples of hormones include, but are not limited to, luteinizing hormone releasing hormone (LHRH), growth hormone (GH), growth hormone releasing hormone, ACTH, somatostatin, somatotropin, somatomedin, parathyroid hormone, hypothalamic releasing factors, insulin, glucagon, enkephalins, vasopressin, calcitonin, heparin, low molecular weight heparins, heparinoids, synthetic and natural opioids, insulin thyroid stimulating hormones, and endorphins. Examples of β-interferons include, but are not limited to, interferon β1-a and interferon β1-b.

The compositions of the invention can comprise an alkylating agent. Examples of alkylating agents include, but are not limited to nitrogen mustards, ethylenimines, methylmelamines, alkyl sulfonates, nitrosoureas, triazenes, mechlorethamine, cyclophosphamide, ifosfamide, melphalan, chlorambucil, hexamethylmelaine, thiotepa, busulfan, carmustine, streptozocin, dacarbazine and temozolomide.

The compositions of the invention can comprise an immunomodulatory agent, including but not limited to methothrexate, leflunomide, cyclophosphamide, cyclosporine A, macrolide antibiotics (e.g., FK506 (tacrolimus)), methylprednisolone (MP), corticosteroids, steroids, mycophenolate mofetil, rapamycin (sirolimus), mizoribine, deoxyspergualin, brequinar, malononitriloamindes (e.g., leflunamide), T cell receptor modulators, and cytokine receptor modulators, peptide mimetics, and antibodies (e.g., human, humanized, chimeric, monoclonal, polyclonal, Fvs, ScFvs, Fab or F(ab)$_2$ fragments or epitope binding fragments), nucleic acid molecules (e.g., antisense nucleic acid molecules and triple helices), small molecules, organic compounds, and inorganic compounds. In particular, immunomodulatory agents include, but are not limited to, methothrexate, leflunomide, cyclophosphamide, cytoxan, Immutan, cyclosporine A, minocycline, azathioprine, antibiotics (e.g., FK506 (tacrolimus)), methylprednisolone (MP), corticosteroids, steroids, mycophenolate mofetil, rapamycin (sirolimus), mizoribine, deoxyspergualin, brequinar, malononitriloamindes (e.g., leflunamide), T cell receptor modulators, and cytokine receptor modulators. Examples of T cell receptor modulators include, but are not limited to, anti-T cell receptor antibodies (e.g., anti-CD4 antibodies (e.g., cM-T412 (Boehringer), IDEC-CE9.Is (IDEC and SKB), mAb 4162W94, Orthoclone and OKTcdr4a (Janssen-Cilag)), anti-CD3 antibodies (e.g., Nuvion (Product Design Labs), OKT3 (Johnson & Johnson), or Rituxan (IDEC)), anti-CD5 antibodies (e.g., an anti-CD5 ricin-linked immunoconjugate), anti-CD7 antibodies (e.g., CHH-380 (Novartis)), anti-CD8 antibodies, anti-CD40 ligand monoclonal antibodies (e.g., IDEC-131 (IDEC)), anti-CD52 antibodies (e.g., CAMPATH 1H (Ilex)), anti-CD2 antibodies, anti-CD1 la antibodies (e.g., Xanelim (Genentech)), and anti-B7 antibodies (e.g., IDEC-114) (IDEC))) and CTLA4-immunoglobulin. In a specific embodiment, a T cell receptor modulator is a CD2 antagonist. In other embodiments, a T cell receptor modulator is not a CD2 antagonist. In another specific embodiment, a T cell receptor modulator is a CD2 binding molecule, preferably MEDI-507. In other embodiments, a T cell receptor modulator is not a CD2 binding molecule.

In another embodiment, a composition of the invention can comprise a crosslinking agent, e.g., riboflavin.

In various embodiments, the biomaterial, e.g., umbilical cord membrane or umbilical cord biomaterial may comprise at least 0.1, 0.2, 0.3, 0.4, 0.5, 0.6, 0.7, 0.8, 0.9, 1, 2, 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 200, 300, 400, 500, 600, 700, 800, 900, 100, 1250, 1500, 2000, 2500, 300, 3500, 4000, 4500, 5000, 5500, 6000, 6500, 7000, 7500, 8000, 8500, 9000, 9500, 10000, 20000, 30000, 40000, 50000, 60000, 70000, 80000, 90000, 100000, 200000, 300000, 400000, 500000, 600000, 700000, 800000, 900000 or at least 1000000 nanograms of a bioactive compound. In another embodiment, the placental biomaterial, e.g., umbilical cord membrane or umbilical cord biomaterial may be coated with, or impregnated with, no more than 0.1, 0.2, 0.3, 0.4, 0.5, 0.6, 0.7, 0.8, 0.9, 1, 2, 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 200, 300, 400, 500, 600, 700, 800, 900, 100, 1250, 1500, 2000, 2500, 300, 3500, 4000, 4500, 5000, 5500, 6000, 6500, 7000, 7500, 8000, 8500, 9000, 9500, 10000, 20000, 30000, 40000, 50000, 60000, 70000, 80000, 90000, 100000, 200000, 300000, 400000, 500000, 600000, 700000, 800000, 900000 or at least 1000000 nanograms of a bioactive compound.

5.2. Methods of Use

The invention further provides methods of using the compositions described herein.

In one embodiment, the invention provides a method of treatment of an ocular condition comprising contacting said condition with a solution of the invention, e.g., a placental tissue solution, an umbilical cord tissue solution, or combination thereof. For example, the solutions described herein can be used in any ocular condition in which the introduction of placental tissue or umbilical cord tissue, e.g., amniotic membrane, umbilical cord membrane, or amniotic membrane or umbilical membrane components, would be useful to encourage ocular tissue repair, regrowth, or to reduce a symptom, e.g., inflammation of a disorder or condition of an eye or a tissue of an eye. In a specific embodiment, the placental tissue solution is an amniotic membrane solution comprising amniotic membrane components soluble at neutral pH, or acidic and neutral pH or basic and neutral pH. In another specific embodiment, the umbilical cord tissue solution is an umbilical cord membrane solution comprising soluble umbilical cord membrane and Wharton's jelly components.

In specific embodiments, the ocular condition or symptom thereof is irritation, inflammation, dryness or stickiness or symblepharon. In another specific embodiment, the ocular condition is a discontinuity of the sclera or cornea. Such a discontinuity can be caused accidentally, e.g., an injury, or can be cause deliberately, e.g., during ocular surgery. In another embodiment, the ocular condition is, or is the result of, a congenital defect. In a specific embodiment, the ocular surgery is refractive surgery. In a specific embodiment, refractive surgery is photorefractive keratectomy (PRK), laser-assisted sub-epithelial keratectomy (LASEK) or laser-assisted in situ keratomileusis (LASIK). In another specific embodiment, said ocular surgical procedure is automated lamellar keratoplasty (ALK), laser thermal keratoplasty (LTK), or conductive keratoplasty (CK). In another embodiment, said ocular surgery is a surgery involving the creation of an incision or hole in the eye, e.g., a cataract surgery, a glaucoma surgery, a vitreoretinal surgery.

Administration of the solution of the invention to the ocular condition can be done a single time or a plurality of times. Administration can be performed as needed, e.g., hourly; once, twice, three times or more daily; weekly, and the like. Administration of the solution can be a sole method of treatment, or can be part of a plurality of treatments administered at the same time or separately.

In one embodiment, the solution of the invention comprises a crosslinking agent. In a specific embodiment, the crosslinking agent is riboflavin. In a more specific embodiment, the solution of the invention comprises riboflavin at a concentration suitable for enabling or facilitating crosslinking of collagens in the eye in, e.g., ultraviolet light-mediated corneal collagen crosslinking. The solution, comprising riboflavin, can be used in the eye to treat any condition in which the cornea of the eye would benefit from increased mechanical strength. Such a condition can be, for instance, keratoconus or corneal ectasia. The solution comprising riboflavin can also be used as an adjunct to a corneal surgery or other ocular procedure such as, e.g., intracorneal ring implantation, conductive keratoplasty, LTK, orthokeratoplasty, prevention of central island, extended PRK, EpiLASIK or LASEK. In a preferred embodiment, the cornea has a pachymetry (thickness) of at least 400 micrometers.

In one embodiment, such crosslinking is accomplished as follows. An eye is treated with an anesthetic, e.g., proparacaine 0.5%. A solution of the invention, comprising riboflavin, is then applied to the eye. Within about 20 minutes, the eye is exposed to UVA light at, e.g., about 370 nm fluence at about 3 mW/cm$^2$. The solution comprising riboflavin is applied to the eye dropwise about every 3 minutes during UVA exposure. Variations of this method will be apparent to those of skill in the art.

In one embodiment, the invention provides a bandage contact lens, wherein the contact lens comprises a composition of the invention, e.g., has been soaked or rehydrated in a solution of the invention, or coated with a composition of the invention (e.g., a gel or paste). In a specific embodiment, the bandage contact lens comprises a low water (i.e., <50% water) nonionic polymer lens, a high water (≧50% water) nonionic polymer lens, a low-water ionic polymer lens or a high-water ionic polymer lens. In a more specific embodiment, the low-water nonionic polymer lens comprises a teflicon, tetrafilcon A, crofilcon, helfilcon A&B, mafilcon, polymacon, hioxifilcon B, or lotrafilcon A lens. In another more specific embodiment, the high-water nonionic polymer lens comprises a lidofilcon A, lidofilcon B, surfilcon A, netrafilcon A, hefilcon C, alfafilcon A, omafilcon A, vasurfilcon A, hioxifilcon A, nelfilcon A, hilafilcon A, or hilafilcon B lens. In another specific embodiment, the low-water ionic polymer lens comprises a bufilcon A, deltafilcon A, or phemfilcon lens. In another specific embodiment, the high-water ionic polymer lens comprises a bufilcon A, perfilcon A, stafilcon A, focofilcon A, ocufilcon B, ocufilcon C, ocufilcon D, ocufilcon E, ocufilcon F, phemfilcon A, methafilcon A, methafilcon B, or vilfilcon A lens. In another specific embodiment, the contact lens is made from biomaterial derived from placental tissue, or umbilical cord tissue, e.g., amniotic membrane, chorion, amnion chorion, umbilical cord membrane, umbilical membrane combined with Wharton's jelly, or the like. In a more specific embodiment, the contact lens is made from biomaterial which is decellularized and dehydrated according to the methods described herein. In another specific embodiment, the contact lens has a hole in the center sufficient to allow a wearer to see clearly for at least a portion of the user's visual field.

In another embodiment, the bandage contact lens comprises collagen, wherein the collagen is crosslinked by riboflavin. Such a bandage contact lens can be made, e.g., by immersing the contact lens in a solution of the invention, wherein the solution comprises riboflavin, and exposing the lens to ultraviolet light (UVA) for a time sufficient for the UVA to crosslink a plurality of the collagens in the lens.

In another embodiment, the invention provides a bandage or wound dressing comprising a composition, e.g., a solution, of the invention. Such a bandage can comprise, for example, a composition of the invention in a gel that can be contacted with the site of a wound, injury, or other discontinuity in, e.g., the skin.

The invention further provides use of the compositions of the invention, e.g., suspensions, solutions, slurries, pastes or gels, in wound healing. For example, the invention provides a method of treating an injury, wound or discontinuity in a tissue of an individual comprising contacting said injury, wound or discontinuity with a composition, e.g., gel or paste, of the invention. In various embodiments, the wound, injury or discontinuity is a laceration, scrape, thermal or chemical burn, incision, puncture, wound caused by a projectile, and the like. Such wounds can be accidental or deliberate, e.g., wounds caused during or as an adjunct to a surgical procedure. Preferably, the wound, injury or discontinuity is closed prior to contacting with the gel or paste of the invention.

In other embodiments, a composition of the invention, e.g., gel or paste, is used as a filler, e.g., for tissue removed during surgery or lost to injury.

In other embodiments, the composition of the invention, e.g., gel or paste, ointment, cream, and the like, comprises a moisturizer or emollient, and is used as a skin softener or soothing agent, e.g., a soothing agent for sunburn.

4.3 Kits

The present invention further provides kits comprising the placental or umbilical cord tissue compositions described herein.

In one embodiment, the invention provides a kit comprising a composition of the invention, e.g., a composition comprising placental tissue components or umbilical cord components soluble in aqueous solution at neutral pH and substantially lacking placental tissue components or umbilical cord components insoluble in aqueous solution at neutral pH, in an appropriately labeled container. In certain embodiments, such kits comprise one or more individually labeled containers containing unit-dosage or multi-dosage aliquots of the composition, useful for administering a defined amount of the composition to an individual. The kit can additionally comprise instructions for administering the compositions of the invention to an individual, including, e.g., instructions on the frequency and dose of administration.

In a more specific embodiment, the invention provides a kit for the treatment of an ocular condition. The kit may comprise a placental or umbilical cord tissue composition of the invention, and any other medical device that would facilitate treatment of an ocular condition treatable with the composition. In a specific embodiment, the kit additionally comprises a bandage contact lens, and includes instructions for use of the bandage contact lens in combination with the placental or umbilical cord tissue composition for the treatment of an ocular condition. In one embodiment, the kit comprises instructions for contacting a tissue of an eye of an individual having or affected by an ocular condition with the composition. In a more specific embodiment, the kit comprises a bandage contact lens, wherein the bandage contact lens comprises a composition of the invention, e.g., has been soaked or rehydrated in a solution of the invention, or coated with a composition of the invention (e.g. a gel or paste). In another specific embodiment, the kit comprises instructions for contacting a tissue of an eye of an individual having or affected by an ocular condition with the bandage contact lens. In another specific embodiment, the kit additionally comprises a crosslinking agent, e.g. riboflavin.

In another specific embodiment, the invention provides a kit for dressing or healing a wound. For example, the kit may comprise one or more bandages comprising a composition, e.g. a solution of the invention. Preferably, the bandage is individually wrapped in, e.g., a peel wrapper or other easily manipulable and openable packaging.

The container in which kit components are handled and sold is preferably labeled per applicable Food and Drug Administration standards.

6. EXAMPLES

6.1. Example 1

PH Shifting Method of Making an Umbilical Cord or Amniotic Membrane Solution

This Example demonstrates a pH shifting method of preparing a suspension or solution of the invention.

6.1.1. Example Method 1

A cleaned, substantially bloodless (exsanguinated) placenta from a normal birth is obtained. The amniotic membrane is removed, roughly chopped, and placed in a volume of a 0.9% phosphate-buffered saline solution containing 10 mM EDTA and 10 mM EGTA, at a ratio of about 100 ml solution for every gram of tissue, at 4° C. The solution is acidified to about pH 4.5 using glacial acetic acid. The pH of the solution is determined using a standard pH meter. The solution and amniotic membrane is placed into a blender, and the amniotic membrane is homogenized for one minute at the highest setting to produce an amniotic membrane suspension. The acidified suspension is allowed to stand at 4° C. for 24 hours. After 24 hours, the suspension is brought to about pH 7.4 with 10N NaOH, and divided into culture bottles suitable for use in a swinging bucket centrifuge rotor. The suspension is centrifuged at 4° C. for 10 minutes at 8000 g to produce a supernatant. The supernatant is dialyzed over a semipermeable membrane against about 20 volumes of deionized water, and stored for further use.

6.1.2. Example Method 2

An umbilical cord is obtained from a cleaned, substantially bloodless (exsanguinated) placenta from a normal birth. Umbilical cord veins are removed with a vein stripper, or are removed by longitudinally cutting the umbilical cord to expose the veins for removal. The umbilical cord membrane and Wharton's jelly is cut into sections of approximately 10 cm to 15 cm in length. The umbilical cord is then rinsed in cold 0.9% saline, and placed in a 0.9% phosphate-buffered saline solution containing 10 mM EDTA and 10 mM EGTA, at a ratio of about 100 ml solution for every gram of tissue, at 4° C. The solution is acidified to about pH 4.5 using glacial acetic acid. The pH of the solution is determined using a standard pH meter. The solution and umbilical cord is placed into a blender, and the umbilical cord is homogenized for one minute at the highest setting to produce an umbilical cord suspension. The acidified suspension is allowed to stand at 4° C. for 24 hours. After 24 hours, the suspension is brought to about pH 7.4 with 10N NaOH, and divided into four culture bottles suitable for use in a swinging bucket centrifuge rotor. The suspension is centrifuged at 4° C. for 10 minutes at 5000 g to produce a supernatant. The supernatant is optionally centrifuged again at 4° C. and 10000 g. The supernatant is dialyzed over a semipermeable membrane against 20 volumes of deionized water, and stored for further use.

6.2. Example 2

Solutions, Gels and Pastes

6.2.1. Amniotic Membrane Solution

This Example demonstrates a method of obtaining an amniotic membrane and the production of a solution of the invention made from amniotic membrane.

A single placenta from a full-term placenta is obtained with donor consent. The donor is pre-screened for viral pathogens including hepatitis A virus, hepatitis B virus, Hepatitis C virus, human immunodeficiency virus types 1 and 2, and cytomegalovirus.

Following normal birth, the placenta, umbilical cord and umbilical cord blood are spontaneously expelled from the contracting uterus. The placenta, umbilical cord, and umbilical cord blood are collected following birth. The materials are transported to a laboratory and processed under aseptic conditions in a clean room having a HEPA filtration system that is turned on at least one hour prior to processing. Gloves (sterile or non-sterile, as appropriate) are worn at all times while handling the placenta. All unused (waste) segments of the amnion/chorion and contaminated liquids generated during tissue processing are disposed of as soon as feasible.

A sterile field is set up with sterile Steri-Wrap sheets and the following instruments and accessories for processing were placed on it: sterile tray pack; sterile cell scraper; sterile scalpel; and a disinfected processing tray.

The placenta is removed from the transport container and placed onto the disinfected stainless steel tray. Using surgical clamps and scissors, the umbilical cord is cut off approximately 2 inches from the placental disc. The umbilical cord is placed into a separate sterile container for further processing.

Starting from the edge of the placental membrane, the amnion is separated from the chorion using blunt dissection with fingers. This is done prior to cutting the membrane. After the amnion is separated from the entire surface of the chorion and placental disc, the amniotic membrane is cut around the umbilical cord stump with scissors and detached from the placental disc. If separation of the amnion and chorion is not possible without tearing the tissue, the amnion and chorion are cut from the placental disc as one piece and then peeled apart. The chorion is placed into a separate specimen container to be utilized for other projects.

The amniotic membrane is optionally decellularized prior to production of an amniotic membrane solution. In decellularization, the amniotic membrane is removed from the rinsing tray, and excess fluid is gently squeezed out with fingers. The membrane is optionally scraped with a cell scraper and rinsed with sufficient sterile water to effect removal of substantially all visible cell material. The amniotic membrane is transferred to a new container, which is then filled up to the 150 ml mark with decellularizing solution (1% deoxycholic acid) ensuring that all of the amniotic membrane is covered. The container is placed in the bin on the rocking platform. The rocking platform is turned on and the membrane was agitated in decellularizing solution at 4° C. for seven days. After decellularization, a new sterile field is set up with new sterile instruments and disinfected tray in a same manner as above. The rocking platform is turned off and the membrane is removed from the container. The membrane is placed into a new sterile stainless steel processing tray, and sterile 0.9% NaCl solution is added to cover the bottom of the tray. Using a new sterile cell scraper, residual decellularization solution and cellular material is removed from both sides of the tissue. This step is repeated as many times as needed to remove as much as possible of visible residual cellular material from the entire surface on both sides. The membrane is rinsed with sterile 0.9% NaCl solution in a separate rinsing tray in between cleaning rounds.

The amniotic membrane, either decellularized or comprising cells, is then weighed, and processed according to the pH shifting protocol described in Example 1, using a weight/volume ratio of amniotic membrane to solution of 1 g:10 ml.

6.2.2. Umbilical Cord Suspension and Solution

The following example demonstrates a method of obtaining an umbilical cord suspension or solution useful for medical, e.g., ocular purposes.

Human umbilical cord (HUC) harvesting. The umbilical cord is separated from the placental disc, and rinsed in a sterile saline solution. The umbilical cord is sectioned into pieces of about 10 cm to about 15 cm in length and is squeezed to remove umbilical cord blood. The umbilical cord is then slit or cut longitudinally using a pair of surgical scissors so that the two arteries and one vein are exposed. The vessels are then removed with a forceps. The umbilical cord membrane, including Wharton's jelly, is then rinsed in cold saline or other balanced salt solution at neutral pH. The solution optionally comprises one or more antibiotics. The umbilical cord membrane can be further processed immediately, or can be stored in a refrigerator for up to about 72 hours in a sterile buffered saline solution, such as 0.9% sterile NaCl solution.

Homogenization of HUC at neutral pH. The following procedures are all carried out at 4° C. and neutral pH (approximately 7.4) under sterile conditions. Umbilical cord membrane is cut into small pieces and weighed. Sterile buffer, and optionally antibiotics, are then added to the chamber of a homogenizer to reach the desired weight to volume ratio (w/v) of 1:5. The membrane pieces are then homogenized to produce an umbilical cord membrane suspension. Homogenization is repeated as necessary in order to obtain a visibly homogenous suspension without raising the temperature above about 4° C. The resulting suspension can be used without further treatment.

The homogenate is centrifuged for 10 minutes at 4° C. and 3500 rpm and then the supernatant is further centrifuged for another 5 minutes at 10000 rpm to get rid of any undesired particulate matter present in the extract to produce an umbilical cord solution.

The obtained umbilical cord membrane solution is analyzed by a Lowry assay to quantify the total protein amount present in the homogenate. The solution is then filtered through 0.45 micron filters under a sterile hood, packaged into small vials and stored at 4° C. until used.

6.2.3. Amniotic Membrane Paste

This example demonstrates two methods of obtaining an amniotic membrane paste.

An amniotic membrane, obtained in the manner described in Section 5.2.1, above, is homogenized and solubilized in the manner described in Example 1. The resulting amniotic membrane solution is dehydrated using a vacuum dehydration apparatus at about 4° C. Dehydration is continued until the water in the solution is substantially removed and the remaining amniotic membrane material appears dry by visual inspection. The mass of the amniotic membrane material is determined, and water or buffer is then added to the amniotic membrane matter to achieve a water content of about 3% to about 10% by weight. The water and amniotic membrane material are thoroughly mixed to form a paste.

In a variation of the above method, the amniotic membrane material is supplemented by an amount of purified collagen not to exceed 100 times the weight of the amniotic membrane material obtained from the amniotic membrane solution, and water is added to as to achieve between 3% and 10% water by weight. The water, amniotic membrane material and purified collagen are thoroughly mixed to form a paste.

6.2.4. Umbilical Membrane Paste

This example demonstrates two methods of obtaining an umbilical cord paste.

An umbilical cord membrane comprising Wharton's jelly, obtained in the manner described in Section 5.2.2, above, is homogenized and solubilized in the manner described in Example 1. The resulting umbilical cord solution is dehydrated using a vacuum dehydration apparatus at about 4° C. Dehydration is continued until the water in the solution is substantially removed and the remaining umbilical cord material appears dry by visual inspection. The mass of the umbilical cord material is determined, and water or buffer is then added to the umbilical cord material to achieve a water content of about 3% to about 10% by weight. The water and umbilical cord material are thoroughly mixed to form a paste.

In a variation of the above method, the umbilical cord material is supplemented by an amount of purified collagen not to exceed 100 times the weight of the umbilical cord material obtained from the umbilical cord solution, and water is added to as to achieve between 3% and 10% water by weight. The water, umbilical cord material and purified collagen are thoroughly mixed to form a paste.

6.2.5. Umbilical Cord Gel

This example demonstrates a method of producing a gel from umbilical cord.

An umbilical cord membrane comprising Wharton's jelly, obtained in the manner described in Section 5.2.2, above, is homogenized and solubilized in the manner described in Example 1. The resulting umbilical cord solution is dehydrated using a vacuum dehydration apparatus at about 4° C. Dehydration is continued until the water in the solution is substantially removed and the remaining umbilical cord material appears dry by visual inspection. The mass of the umbilical cord material is determined, and a gelling compound is added in a weight/weight ratio to the umbilical cord material of about 10:1. Water is then added to the umbilical cord material and gelling compound in an amount that brings the water content of the resulting gel to about 60% to about 99% by weight.

In a variation of the above method, the umbilical cord material is supplemented with purified collagen in a weight not to exceed 100 times the weight of the umbilical cord material obtained from the umbilical cord solution. Water is added to the umbilical cord material, purified collagen, and gelling agent to bring the water content of the resulting gel to 60% to about 99% by weight.

6.2.6. Combination Compositions

This Example demonstrates methods of producing combinations of compositions made from placental tissue and umbilical cord tissue.

A solution of the invention is produced as follows. A solution comprising amniotic membrane components is made according to the method described in Section 5.2.1, above, and a solution comprising umbilical cord membrane components is made according to the method described in Section 5.2.2, above. The two solutions are combined in a ratio of from about 1:10 to about 10:1 by volume, and mixed thoroughly. Alternatively, the protein content of each solution is determined, and the two solutions re combined in a ratio of from about 1:10 to about 10:1 by protein content. The resulting solution is centrifuged to remove visible solid matter and stored at 4° C. for later use.

A solution of the invention is produced as follows. A solution comprising amniotic membrane components is made according to the method described in Section 5.2.1, and is mixed thoroughly with an umbilical cord membrane paste containing purified collagen as described in Section 5.2.4, above. The resulting solution is centrifuged to remove visible solid matter and stored at 4° C. for later use.

EQUIVALENTS

The present invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

Various publications, patents and patent applications are cited herein, the disclosures of which are incorporated by reference in their entireties.

What is claimed is:

1. A composition comprising placental tissue components soluble in aqueous solution at acidic and neutral pH, and substantially lacking placental tissue components insoluble in aqueous solution at acidic and neutral pH, wherein the composition is prepared according to the following method:
   (a) contacting placental tissue with an acidic solution;
   (b) bringing the solution to neutral pH; and
   (c) removing insoluble matter within said solution to form the composition.

2. The composition of claim 1, wherein said placental tissue is amniotic membrane (AM).

3. The composition of claim 1, wherein the composition is formulated as a liquid, gel, paste, slurry, cream or ointment.

4. The composition of claim 3, wherein the composition is an ophthalmologically-acceptable liquid.

5. The composition of claim 4, wherein said liquid comprises saline solution, glycerin, hypromellose, or polyethylene glycol.

6. The composition of claim 1 comprising at least 10% placental components by weight.

7. The composition of claim 1, wherein the composition is formulated as a lyophilized composition.

8. The composition of claim 1 further comprising an ophthalmologically-acceptable lubricant.

9. The composition of claim 1 further comprising one or more of an anti-inflammatory compound, an analgesic, an anesthetic or an immune-suppressing agent.

10. The composition of claim 1 further comprising riboflavin.

11. The composition of claim 10, wherein the composition comprises collagen crosslinked with the riboflavin.

12. The composition of claim 1, wherein the insoluble matter in said solution is removed following step (a).

13. The composition of claim 12, wherein the method further comprises removal of the insoluble matter in said solution following step (b).

14. The composition of claim 1, wherein the placental tissue is substantially bloodless.

15. The composition of claim 1, wherein said acidic solution is an acetic acid solution.

16. The composition of claim 1, wherein said acidic solution is between about pH 4.5 and about pH 6.

17. The composition of claim 1, wherein said placental tissue is disrupted at a temperature of between about the freezing point of said solution to about 10° C.

18. The composition of claim 17 comprising decellularizing said placental tissue prior to said disruption.

19. The composition of claim 1, additionally comprising adjusting the water content of the solution to no greater than about 50%.

20. The composition of claim 1, wherein the insoluble matter is removed by centrifugation.

* * * * *